US010828350B1

(12) United States Patent
Bermudes et al.

(10) Patent No.: US 10,828,350 B1
(45) Date of Patent: Nov. 10, 2020

(54) TOPICAL AND ORALLY ADMINISTERED PROTEASE INHIBITORS AND BACTERIAL VECTORS FOR THE TREATMENT OF DISORDERS AND METHODS OF TREATMENT

(71) Applicant: David Gordon Bermudes, Woodland Hills, CA (US)

(72) Inventors: David Gordon Bermudes, Woodland Hills, CA (US); David Quintero, Northridge, CA (US)

( * ) Notice: Subject to any disclaimer, the term of this patent is extended or adjusted under 35 U.S.C. 154(b) by 33 days.

(21) Appl. No.: 15/679,896

(22) Filed: Aug. 17, 2017

Related U.S. Application Data

(62) Division of application No. 14/624,460, filed on Feb. 17, 2015, now Pat. No. 9,737,592.

(60) Provisional application No. 61/939,992, filed on Feb. 14, 2014, provisional application No. 61/939,740, filed on Feb. 14, 2014, provisional application No. 61/940,019, filed on Feb. 14, 2014.

(51) Int. Cl.
*A61K 38/55* (2006.01)
*C12Q 1/37* (2006.01)
*C07K 14/81* (2006.01)

(52) U.S. Cl.
CPC .......... *A61K 38/55* (2013.01); *C07K 14/81* (2013.01); *C12Q 1/37* (2013.01); *G01N 2333/81* (2013.01); *G01N 2500/04* (2013.01); *G01N 2500/10* (2013.01)

(58) Field of Classification Search
CPC .............................. A61K 38/55; C12Q 1/37
See application file for complete search history.

(56) References Cited

U.S. PATENT DOCUMENTS

| | | |
|---|---|---|
| D320,325 S | 10/1991 | Barfield |
| 5,143,830 A | 9/1992 | Holland et al. |
| 5,278,049 A | 1/1994 | Baker et al. |
| 5,354,675 A | 10/1994 | Iida et al. |
| 5,399,490 A | 3/1995 | Balganesh et al. |
| 5,466,463 A | 11/1995 | Ford |
| 5,466,672 A | 11/1995 | Kushnaryov et al. |
| 5,495,001 A | 2/1996 | McGrogan et al. |
| 5,569,597 A | 10/1996 | Grimsley et al. |
| 5,635,484 A | 6/1997 | Ayres et al. |
| 5,712,369 A | 1/1998 | Old et al. |
| 6,030,780 A | 2/2000 | Vinkemeier et al. |
| 6,037,526 A | 3/2000 | Grimsley et al. |
| 6,080,849 A | 6/2000 | Bermudes et al. |
| 6,190,657 B1 | 2/2001 | Pawelek et al. |
| 6,207,156 B1 | 3/2001 | Kuchroo et al. |
| 6,232,110 B1 | 5/2001 | Pallas et al. |
| 6,329,002 B1 | 12/2001 | Kim et al. |
| 6,355,790 B1 | 3/2002 | Rosenblatt et al. |
| 6,376,234 B1 | 4/2002 | Grimsley et al. |
| 6,447,784 B1 | 9/2002 | Bermudes et al. |
| 6,475,482 B1 | 11/2002 | Bermudes et al. |
| 6,548,287 B1 | 4/2003 | Powell et al. |
| 6,605,697 B1 | 8/2003 | Kwon et al. |
| 6,638,912 B2 | 10/2003 | Bhatnagar et al. |
| 6,685,935 B1 | 2/2004 | Pawelek et al. |
| 6,743,893 B2 | 6/2004 | Engler et al. |
| 6,841,535 B2 | 1/2005 | Divita et al. |
| 6,863,894 B2 | 3/2005 | Bermudes et al. |
| 6,923,972 B2 | 8/2005 | Bermudes et al. |
| 6,962,696 B1 | 11/2005 | Bermudes et al. |
| 7,354,592 B2 | 4/2008 | Bermudes et al. |
| 7,358,084 B2 | 4/2008 | Kolkman |
| 7,390,646 B2 | 6/2008 | Andino-Pavlovsky et al. |
| 7,452,531 B2 | 11/2008 | Bermudes et al. |
| 7,514,089 B2 | 4/2009 | Bermudes et al. |
| 7,635,682 B2 | 12/2009 | Denmeade et al. |
| 7,666,627 B2 | 2/2010 | Gal et al. |
| 7,700,349 B2 | 4/2010 | Romaine et al. |
| 7,700,830 B2 | 4/2010 | Corbin et al. |
| 7,705,195 B2 | 4/2010 | French et al. |
| 7,803,918 B2 | 9/2010 | van der Hoek |

(Continued)

FOREIGN PATENT DOCUMENTS

| | | |
|---|---|---|
| EP | 0973911 A1 | 1/2000 |
| EP | 1513924 A1 | 3/2005 |

(Continued)

OTHER PUBLICATIONS

Wikstrom, 1983, Detection of Microbial Proteolytic Activity by a Cultivation Plate Assay in Which Different Proteins Adsorbed to a Hydrophobic Surface Are Used as Substrates, Applied and Environmental Microbiology, 45(2): 393-400.*

Vermelho et al., 1996, Detection of Extracellular Proteases from Microorganisms on Agar Plates, Mem Inst Oswaldo Cruz, 91(6): 755-760.*

Kasana et al., 2011, Microbial proteases: Detection, production, and genetic improvement, Critical Reviews in Microbiology, 37(3): 262-276.*

(Continued)

*Primary Examiner* — Amber D Steele
(74) *Attorney, Agent, or Firm* — Hoffberg & Associates; Steven M. Hoffberg

(57) ABSTRACT

The present invention provides purified protease inhibitors derived from microorganisms alone or in combination with bacteriocins and/or antibodies. The protease inhibitors may also be expressed by microbiome or probiotic microorganisms alone or in combination with bacteriocins and/or antibodies. The invention also provides methods and compositions for improving the expression of endogenous or heterologous protease inhibitors alone or in combination with bacteriocins and/or antibodies. The invention is useful for treating a variety of inflammatory disorders including acne, psoriasis, eczema, atopic dermatitis and inflammatory bowel disease.

20 Claims, 4 Drawing Sheets

Specification includes a Sequence Listing.

(56) References Cited

U.S. PATENT DOCUMENTS

| | | | |
|---|---|---|---|
| 7,888,321 B2 | 2/2011 | Cooper et al. |
| 7,892,803 B2 | 2/2011 | Tanner et al. |
| 7,892,825 B2 | 2/2011 | Barr et al. |
| 7,947,822 B2 | 5/2011 | Nabel et al. |
| 7,964,362 B2 | 6/2011 | Lee et al. |
| 7,989,202 B1 | 8/2011 | Mach et al. |
| 8,030,542 B2 | 10/2011 | Corbin et al. |
| 8,062,885 B2 | 11/2011 | Mach et al. |
| 8,101,349 B2 | 1/2012 | Garcia et al. |
| 8,101,826 B2 | 1/2012 | Romano |
| 8,119,354 B2 | 2/2012 | Katanaev |
| 8,173,397 B2 | 5/2012 | Gal et al. |
| 8,206,700 B2 | 6/2012 | Horwitz et al. |
| 8,236,315 B2 | 8/2012 | Lazarides et al. |
| 8,241,623 B1 | 8/2012 | Bermudes |
| 8,244,484 B2 | 8/2012 | Lee et al. |
| 8,323,961 B2 | 12/2012 | Nabel et al. |
| 8,440,207 B2 | 5/2013 | Bermudes |
| 8,445,650 B2 | 5/2013 | Simpson et al. |
| 8,524,220 B1 | 9/2013 | Bermudes |
| 8,603,824 B2 | 12/2013 | Ramseier et al. |
| 8,623,350 B1 | 1/2014 | Bermudes |
| 8,628,782 B2 | 1/2014 | Berkower |
| 8,647,642 B2 | 2/2014 | Bermudes |
| 8,686,218 B2 | 4/2014 | Romaine et al. |
| 8,741,313 B2 | 6/2014 | Sable et al. |
| 8,748,373 B2 | 6/2014 | Chai et al. |
| 8,759,086 B2 | 6/2014 | Mach et al. |
| 8,771,669 B1 | 7/2014 | Bermudes |
| 8,771,671 B2 | 7/2014 | Spencer et al. |
| 8,791,237 B2 | 7/2014 | Paterson et al. |
| 8,821,893 B2 | 9/2014 | Dattwyler et al. |
| 8,835,107 B2 | 9/2014 | Van Der Hoek |
| 8,853,362 B2 | 10/2014 | Tissot et al. |
| 8,906,662 B2 | 12/2014 | Nataro et al. |
| 8,920,809 B2 | 12/2014 | Dirienzo |
| 8,926,993 B2 | 1/2015 | Dubensky, Jr. et al. |
| 8,956,859 B1 | 2/2015 | Bermudes |
| 8,962,816 B2 | 2/2015 | Ertl et al. |
| 8,969,542 B2 | 3/2015 | Buyse et al. |
| 8,999,949 B2 | 4/2015 | Spencer et al. |
| 9,068,187 B1 | 6/2015 | Bermudes |
| 9,109,229 B2 | 8/2015 | Ramseier et al. |
| 9,161,974 B2 | 10/2015 | Dubensky et al. |
| 9,187,762 B2 | 11/2015 | Albert et al. |
| 9,198,960 B2 | 12/2015 | Dubensky, Jr. et al. |
| 9,200,251 B1 | 12/2015 | Bermudes |
| 9,200,289 B1 | 12/2015 | Bermudes |
| 9,206,456 B2 | 12/2015 | Lenormand |
| 2001/0029024 A1 | 10/2001 | Kodadek |
| 2002/0016982 A1 | 2/2002 | Romaine et al. |
| 2002/0026655 A1 | 2/2002 | Bermudes et al. |
| 2002/0106380 A1 | 8/2002 | Hung et al. |
| 2002/0107374 A1 | 8/2002 | Pallas et al. |
| 2002/0123053 A1 | 9/2002 | Luo et al. |
| 2003/0059400 A1 | 3/2003 | Szalay |
| 2003/0092066 A1 | 5/2003 | Vinkemeier et al. |
| 2003/0106096 A1 | 6/2003 | Barry |
| 2003/0109026 A1 | 6/2003 | Bermudes et al. |
| 2003/0113293 A1 | 6/2003 | Bermudes et al. |
| 2003/0114372 A1* | 6/2003 | White .................... C07K 14/81 514/14.3 |
| 2003/0115630 A1 | 6/2003 | Romano |
| 2003/0124561 A1 | 7/2003 | Mach et al. |
| 2003/0131372 A1 | 7/2003 | Copenhaver et al. |
| 2003/0131376 A1 | 7/2003 | Okubara et al. |
| 2003/0144490 A1 | 7/2003 | Edwards et al. |
| 2003/0166140 A1 | 9/2003 | Chen et al. |
| 2003/0170276 A1 | 9/2003 | Bermudes et al. |
| 2003/0186416 A1 | 10/2003 | Pallas et al. |
| 2003/0188336 A1 | 10/2003 | Corbin et al. |
| 2003/0203377 A1 | 10/2003 | Milne Edwards et al. |
| 2003/0211476 A1 | 11/2003 | O'Mahony et al. |
| 2004/0013658 A1 | 1/2004 | Fulton et al. |
| 2004/0023282 A1 | 2/2004 | Luo et al. |
| 2004/0038307 A1 | 2/2004 | Lee et al. |
| 2004/0096426 A1 | 5/2004 | Chen et al. |
| 2004/0101531 A1 | 5/2004 | Curtiss et al. |
| 2004/0110939 A1 | 6/2004 | Dumas Milne Edwards et al. |
| 2004/0115788 A1 | 6/2004 | Zheng et al. |
| 2004/0133930 A1 | 7/2004 | Cooper et al. |
| 2004/0180380 A1 | 9/2004 | Lee et al. |
| 2004/0191787 A1 | 9/2004 | Tanner et al. |
| 2004/0219169 A1 | 11/2004 | Bermudes et al. |
| 2004/0229338 A1 | 11/2004 | King |
| 2004/0234956 A1 | 11/2004 | Kabat et al. |
| 2004/0266674 A1 | 12/2004 | Mills et al. |
| 2005/0032157 A1 | 2/2005 | Gal et al. |
| 2005/0036987 A1 | 2/2005 | Pawelek et al. |
| 2005/0055746 A1 | 3/2005 | Michaud et al. |
| 2005/0069911 A1 | 3/2005 | Lee et al. |
| 2005/0070007 A1 | 3/2005 | Romaine et al. |
| 2005/0074463 A1 | 4/2005 | Autran et al. |
| 2005/0084972 A1 | 4/2005 | Barr et al. |
| 2005/0112139 A1 | 5/2005 | Karp |
| 2005/0158295 A1 | 7/2005 | Swiercz et al. |
| 2005/0166274 A1 | 7/2005 | French et al. |
| 2005/0180963 A1 | 8/2005 | Adams et al. |
| 2005/0202535 A1* | 9/2005 | Collier .................... C07K 7/06 435/69.2 |
| 2005/0227917 A1 | 10/2005 | Williams et al. |
| 2005/0241015 A1 | 10/2005 | Mach et al. |
| 2005/0241016 A1 | 10/2005 | Mach et al. |
| 2005/0249706 A1 | 11/2005 | Bermudes et al. |
| 2005/0251885 A1 | 11/2005 | Michaud et al. |
| 2005/0255088 A1 | 11/2005 | Bermudes et al. |
| 2005/0257282 A1 | 11/2005 | Mach et al. |
| 2005/0266560 A1 | 12/2005 | Preuss et al. |
| 2005/0268359 A1 | 12/2005 | Mach et al. |
| 2005/0273882 A1 | 12/2005 | Romano |
| 2005/0281828 A1 | 12/2005 | Bowdish et al. |
| 2006/0009633 A9 | 1/2006 | Dumas Milne Edwards et al. |
| 2006/0014212 A1 | 1/2006 | Benkovic et al. |
| 2006/0024668 A1 | 2/2006 | Hoek |
| 2006/0035270 A1 | 2/2006 | Lee et al. |
| 2006/0035320 A1 | 2/2006 | Tissot et al. |
| 2006/0035371 A1 | 2/2006 | Zheng et al. |
| 2006/0110747 A1 | 5/2006 | Ramseier et al. |
| 2006/0156440 A1 | 7/2006 | Michaud et al. |
| 2006/0160152 A1 | 7/2006 | Vinkemeier et al. |
| 2006/0174357 A1 | 8/2006 | Velander et al. |
| 2006/0182762 A1 | 8/2006 | Maas et al. |
| 2006/0223142 A1 | 10/2006 | Dumas Milne Edwards et al. |
| 2006/0269561 A1 | 11/2006 | Paterson et al. |
| 2006/0275823 A1 | 12/2006 | Kodadek |
| 2006/0275897 A1 | 12/2006 | Nabel et al. |
| 2006/0286639 A1 | 12/2006 | Dumas Milne Edwards et al. |
| 2007/0009489 A1 | 1/2007 | Bermudes et al. |
| 2007/0020327 A1 | 1/2007 | Fikes et al. |
| 2007/0028324 A1 | 2/2007 | Corbin et al. |
| 2007/0059799 A1 | 3/2007 | Sette et al. |
| 2007/0143871 A1 | 6/2007 | French et al. |
| 2007/0298012 A1 | 12/2007 | King et al. |
| 2008/0019994 A1 | 1/2008 | Brunham et al. |
| 2008/0038296 A1 | 2/2008 | Brahmbhatt et al. |
| 2008/0070255 A1 | 3/2008 | Tanner et al. |
| 2008/0085854 A1* | 4/2008 | Barr .................... C07K 14/811 514/20.2 |
| 2008/0090770 A1 | 4/2008 | Belmares et al. |
| 2008/0124355 A1 | 5/2008 | Bermudes |
| 2008/0269070 A1 | 10/2008 | Ramseier et al. |
| 2008/0286306 A1 | 11/2008 | Nabel et al. |
| 2008/0288264 A1 | 11/2008 | Mach et al. |
| 2008/0311081 A1 | 12/2008 | Fruehauf et al. |
| 2009/0019609 A1 | 1/2009 | Romano |
| 2009/0023157 A1 | 1/2009 | Lee et al. |
| 2009/0029369 A1* | 1/2009 | Cottier .................... C12Q 1/37 435/5 |
| 2009/0042248 A1 | 2/2009 | Gal et al. |
| 2009/0042278 A1 | 2/2009 | Barr et al. |
| 2009/0123426 A1 | 5/2009 | Li et al. |
| 2009/0169517 A1 | 7/2009 | Bermudes et al. |
| 2009/0169566 A1 | 7/2009 | Rawlin et al. |
| 2009/0209749 A1 | 8/2009 | Mach et al. |

(56) References Cited

U.S. PATENT DOCUMENTS

| | | |
|---|---|---|
| 2009/0217396 A1 | 8/2009 | Kyrkanides et al. |
| 2009/0232804 A1 | 9/2009 | Lazarides et al. |
| 2009/0239797 A1 | 9/2009 | Cooper et al. |
| 2009/0240073 A1 | 9/2009 | Barry |
| 2009/0246220 A1 | 10/2009 | Ertl et al. |
| 2009/0258935 A1 | 10/2009 | Zheng et al. |
| 2009/0294288 A1 | 12/2009 | May et al. |
| 2009/0297560 A1 | 12/2009 | Dattwyler et al. |
| 2009/0317418 A1 | 12/2009 | Catanzaro et al. |
| 2010/0086546 A1 | 4/2010 | Lee et al. |
| 2010/0111998 A1 | 5/2010 | Nabel et al. |
| 2010/0135961 A1 | 6/2010 | Bermudes |
| 2010/0136048 A1 | 6/2010 | Bermudes |
| 2010/0137162 A1 | 6/2010 | Retallack et al. |
| 2010/0169988 A1 | 7/2010 | Kohli et al. |
| 2010/0184613 A1 | 7/2010 | Lee et al. |
| 2010/0189774 A1 | 7/2010 | Lenormand |
| 2010/0215679 A1 | 8/2010 | Horwitz et al. |
| 2010/0215682 A1 | 8/2010 | Berkower |
| 2010/0239546 A1 | 9/2010 | Fruehauf et al. |
| 2010/0247560 A1 | 9/2010 | Simpson et al. |
| 2010/0261201 A1 | 10/2010 | Katanaev |
| 2010/0272750 A1 | 10/2010 | Buyse et al. |
| 2010/0319087 A1 | 12/2010 | Corbin et al. |
| 2010/0333235 A1 | 12/2010 | Mach et al. |
| 2011/0014701 A1 | 1/2011 | Ghosh |
| 2011/0027349 A1 | 2/2011 | Sable et al. |
| 2011/0065091 A1 | 3/2011 | Van Der Hoek |
| 2011/0189774 A1 | 8/2011 | Mach et al. |
| 2011/0201109 A1 | 8/2011 | Zwaka et al. |
| 2011/0223241 A1 | 9/2011 | Tardi et al. |
| 2011/0257080 A1 | 10/2011 | Chai et al. |
| 2011/0262474 A1 | 10/2011 | Du et al. |
| 2011/0274721 A1 | 11/2011 | Nabel et al. |
| 2011/0275585 A1 | 11/2011 | Brahmbhatt et al. |
| 2011/0277180 A1 | 11/2011 | Romano |
| 2011/0293608 A1 | 12/2011 | Jaffee et al. |
| 2011/0305724 A1 | 12/2011 | Paterson et al. |
| 2012/0027785 A1 | 2/2012 | Dirienzo |
| 2012/0042413 A1 | 2/2012 | Albert et al. |
| 2012/0088314 A1 | 4/2012 | Katanaev |
| 2012/0093773 A1 | 4/2012 | Li et al. |
| 2012/0142080 A1 | 6/2012 | Bermudes |
| 2012/0164687 A1 | 6/2012 | Bereta et al. |
| 2012/0195859 A1* | 8/2012 | Vergnolle ............ A61K 35/74 424/93.2 |
| 2012/0219545 A1 | 8/2012 | Ayuso et al. |
| 2012/0271036 A1 | 10/2012 | Smith et al. |
| 2012/0276132 A1 | 11/2012 | Feng et al. |
| 2012/0308575 A1 | 12/2012 | Guo et al. |
| 2013/0017173 A1 | 1/2013 | Nataro et al. |
| 2013/0028924 A1 | 1/2013 | Ertl et al. |
| 2013/0122043 A1 | 5/2013 | Guimaraes et al. |
| 2013/0129713 A1 | 5/2013 | Rescigno et al. |
| 2013/0202557 A1 | 8/2013 | Li et al. |
| 2013/0209405 A1 | 8/2013 | Curtiss et al. |
| 2013/0269057 A1 | 10/2013 | Fosu-Nyarko et al. |
| 2013/0276168 A1 | 10/2013 | Romaine et al. |
| 2013/0344033 A1* | 12/2013 | Vergnolle ............ A61K 35/74 424/93.2 |
| 2014/0057940 A1 | 2/2014 | Mankowski et al. |
| 2014/0093528 A1 | 4/2014 | Berkower |
| 2014/0155343 A1 | 6/2014 | Brahmbhatt et al. |
| 2014/0162279 A1 | 6/2014 | Ramseier et al. |
| 2014/0162952 A1 | 6/2014 | Katagiri et al. |
| 2014/0173774 A1 | 6/2014 | Pareddy et al. |
| 2014/0173780 A1 | 6/2014 | Pareddy et al. |
| 2014/0220661 A1 | 8/2014 | Bermudes |
| 2014/0227286 A1 | 8/2014 | Jaffee et al. |
| 2014/0287419 A1 | 9/2014 | Althoff et al. |
| 2014/0289906 A1 | 9/2014 | Althoff et al. |
| 2015/0017138 A1 | 1/2015 | Fruehauf et al. |
| 2015/0017204 A1 | 1/2015 | Bermudes |
| 2015/0030573 A1 | 1/2015 | Fruehauf et al. |
| 2015/0044256 A1 | 2/2015 | Dattwyler et al. |
| 2015/0050308 A1 | 2/2015 | van der Hoek |
| 2015/0057191 A1 | 2/2015 | Tissot et al. |
| 2015/0125849 A1 | 5/2015 | Yeh et al. |
| 2015/0132330 A1 | 5/2015 | Garcia-Sastre et al. |
| 2015/0153358 A1 | 6/2015 | Ayuso et al. |
| 2015/0197748 A1 | 7/2015 | Liu et al. |
| 2015/0216965 A1 | 8/2015 | Diamond et al. |
| 2015/0225692 A1 | 8/2015 | Bhatia et al. |
| 2015/0231207 A1 | 8/2015 | Kaspar |
| 2015/0246137 A1 | 9/2015 | Guo et al. |
| 2015/0291667 A1 | 10/2015 | Dirienzo |
| 2015/0337321 A1 | 11/2015 | Mach et al. |
| 2015/0351390 A1 | 12/2015 | Castle et al. |
| 2015/0355172 A1 | 12/2015 | Kraus et al. |

FOREIGN PATENT DOCUMENTS

| | | |
|---|---|---|
| EP | 1655370 A1 | 5/2006 |
| JP | 2009269922 A | 11/2009 |
| WO | WO1991000014 | 1/1991 |
| WO | WO9638159 A1 | 12/1996 |
| WO | WO9640238 A1 | 12/1996 |
| WO | WO1997014782 | 4/1997 |
| WO | WO1999010485 | 3/1999 |
| WO | WO0004919 A2 | 2/2000 |
| WO | WO2000004919 | 2/2000 |
| WO | WO2001014579 | 3/2001 |
| WO | WO0125397 A2 | 4/2001 |
| WO | WO2001025397 | 4/2001 |
| WO | WO02070645 A2 | 9/2002 |
| WO | WO2002070645 | 9/2002 |
| WO | WO03072125 A1 | 9/2003 |
| WO | WO03102168 A1 | 12/2003 |
| WO | WO2004076484 A1 | 9/2004 |
| WO | WO2004103404 A1 | 12/2004 |
| WO | WO2005018332 A1 | 3/2005 |
| WO | WO2005054477 A1 | 6/2005 |
| WO | WO2006010070 A2 | 1/2006 |
| WO | WO2006013441 A2 | 2/2006 |
| WO | WO2006048344 A1 | 5/2006 |
| WO | WO2006116545 A2 | 11/2006 |
| WO | WO2008073148 A2 | 6/2008 |
| WO | WO2008091375 A2 | 7/2008 |
| WO | WO2009014650 A2 | 1/2009 |
| WO | WO2009008116 A2 | 7/2009 |
| WO | WO2009126189 A1 | 10/2009 |
| WO | WO2009139985 A2 | 11/2009 |
| WO | WO2009145956 A2 | 12/2009 |
| WO | WO2009152480 A2 | 12/2009 |
| WO | WO2011086172 A1 | 7/2011 |
| WO | WO2012104025 A2 | 8/2012 |
| WO | WO2012150269 A1 | 11/2012 |
| WO | WO2013067185 A1 | 5/2013 |

OTHER PUBLICATIONS

Quintero et al., 2014, A Culture-Based Method for Determining the production of Secreted Protease Inhibitors, J Microbiol Methods, 100: 105-110.*

Wahyudi et al., 2010, Screening and Characterization of Protease Inhibitors from Marine Bacteria Associated with Sponge *Jaspis* sp., Journal of Biosciences, 17(4): 173-178.*

Stein et al., 2012, One-shot NMR analysis of microbial secretions identifies highly potent proteasome inhibitor, PNAS, 109(45): 18367-18371.*

Sabotic et al., 2012, Microbial and fungal protease inhibitors—current and potential applications, Appl Microbiol Biotechnol, 93: 1351-1375.*

Pellegrini et al., 1984, Natural Protease Inhibitors: Qualitative and Quantitative Assay by Fibrinogen-Agarose Electrophoresis, Analytical Biochemistry, 138: 335-339.*

Braat et al., 2006, A Phase I Trial with Transgenic Bacteria Expressing Interleukin-10 in Crohn's Disease, Clinical Gastroenterology and Hepatology, 4: 754-759.*

Wells et al., 2008, Mucosal delivery of therapeutic and prophylactic molecules using lactic acid bacteria, Nature Reviews: Microbiology, 6: 349-362.*

(56) References Cited

OTHER PUBLICATIONS

Oliver et al., 2002, The mismatch repair system (mutS, mutL and uvrD genes) in Pseudomonas aeruginosa: molecular characterization of naturally occurring mutants, Molecular Microbiology, 43(6): 1641-1650.*
Smith et al., 2010, Broad Spectrum Antibiotic Activity of the Arylomycin Natural Products is Masked by Natural Target Mutations, Chem Biol, 17(11): 1223-1231.*
Von Eiff, 2008, *Staphylococcus aureus* small colony variants: a challenge to microbiologists and clinicians, International Journal of Antimicrobial Agents, 31: 507-510.*
Bermudez-Humaran et al., 2013, Engineering lactococci and lactobacilli for human health, Current Opinion in Microbiology, 16: 278-283.*
Suming Wang, Jinbo Han, Yanfang Wang, Wuyuan Lu, and Chengwu Chi, "Design of peptide inhibitors for furin based on the C-terminal fragment of histone H1.2", Acta Biochim Biophys Sin (2008), vol. 40, Issue 10, p. 848-854.
http://en.wikipedia.org/wiki/Neutrophil (accessed Jul. 1, 2014).
http://en.wikipedia.org/wiki/T-cell (Accessed Jul. 1, 2014).
http://www.uniprot.org/uniprot/Q4GWU5, Q4GWU5 (SFTI1.sub.—HELAN) Reviewed, UniProtKB/Swiss-Prot, Trypsin Inhibitor 1 (SFTI-1) (Accessed Jul. 1, 2014).
http://www.ebi.ac.uk/pdbe-site/pdbemotif/sequence?accessionCode=1o8y (Accessed Jul. 1, 2014).
Marx, Ute C., et al. "Enzymatic cyclization of a potent Bowman-Birk protease inhibitor, sunflower trypsin inhibitor-1, and solution structure of an acyclic precursor peptide." Journal of Biological Chemistry 278.24 (2003): 21782-21789.

* cited by examiner

TOPICAL AND ORALLY ADMINISTERED PROTEASE INHIBITORS AND BACTERIAL VECTORS FOR THE TREATMENT OF DISORDERS AND METHODS OF TREATMENT

CROSS REFERENCE TO RELATED APPLICATIONS

The present application is Divisional of U.S. patent application Ser. No. 14/624,460, filed Feb. 17, 2015, now U.S. Pat. No. 9,737,592, issued Aug. 22, 2017, which is a non-provisional of U.S. Provisional patent application 61/939,992, filed Feb. 14, 2014, and U.S. Provisional patent application 61/939,740, filed Feb. 14, 2014, and of U.S. Provisional patent application 61/940,019, filed Feb. 14, 2014, each of which is expressly incorporated herein by reference in its entirety.

STATEMENT OF GOVERNMENT RIGHTS

This invention was made with government support under 1SC3GM098207 awarded by The National Institutes of Health. The government has certain rights in the invention.

1. BACKGROUND OF THE INVENTION

1.1. Field of the Invention

This invention is generally to the field of therapeutic delivery systems, including topical and oral formulations of human microbiome purified protease inhibitors and probiotic bacteria and/or genetically engineered probiotic bacterial compositions and methods for providing therapeutic protease inhibitors.

2. BACKGROUND OF THE INVENTION

Citation or identification of any reference herein, or any section of this application shall not be construed as an admission that such reference is available as prior art to the present application. The disclosures of each of the publications cited herein, are hereby incorporated by reference in their entirety in this application, and shall be treated as if the entirety thereof forms a part of this application.

Worldwide, inflammatory and hyper-proliferative diseases of the skin, gut, eye, vagina, mouth, nasopharyngeal region and bladder, including cancer, cause substantial morbidity and mortality. Conventional anti-inflammatory drugs such as corticosteroids offer one of the greatest means of preventing or treating inflammation. Unfortunately, many diseases remain without effective therapies. New therapies, including novel therapeutics and novel delivery methods are needed in order to meet the worldwide challenge of inflammation.

Inflammation is involved in a number of disease pathologies, including acne vulgaris, Alzheimer's, ankylosing spondylitis, arthritis (osteoarthritis, rheumatoid arthritis (RA), asthma, atherosclerosis, atopic dermatitis, atrophic vaginitis, autoimmune diseases, bacterial vaginitis, celiac disease, chronic prostatitis, cancer, colitis, Crohn's disease, dermatitis/eczema, diaper rash, "monkey butt", diverticulitis, erythroderma, fibromyalgia, glomerulonephritis, hepatitis, hypersensitivities, inflammatory bowel diseases, interstitial cystitis, irritable bowel syndrome (IBS), lichenoid disorders, lupus erythematous, nephritis, Parkinson's, pelvic inflammatory disease, psoriasis (including flexural, pustular, palmoplantar pustular, nail, acrodermatitis of hallopeau, psoriatic arthritis, and plaque psoriasis), reperfusion injury, rheumatoid arthritis, rosacea, sarcoidosis, sebaceous cysts, systemic lupus erythematous (SLE), Stevens-Johnson syndrome and toxic epidermal necrolysis erythroderma, Netherton syndrome, transplant rejection, ulcerative colitis vasculitis, or chronic condition known as dystrophic epidermolysis bullosa (DEB), which causes severe blistering and can lead to early deaths from skin cancer.

The most important functions of the skin include formation of an effective barrier between the internal and external layers of the organism (Uchida et al., 2011 JPET August 2011 vol. 338 no. 2 443-450.) However, it is also true that because of this effective barrier function, the skin is also difficult to effectively deliver therapeutics. Thus it is apparent that delivery mechanisms that penetrate to the site of the diseased cells or tissues have the potential to overcome present limitations.

The use of live attenuated bacteria as carriers for delivering therapeutics is considered a promising methodology, yet remains without any products approved for clinical use more than 20 years after the concept was first developed (see Kotton and Hohmann 2004, Infection and Immunity 72: 5535-5547 and Roland et al., 2005, Current opinion in Molecular Therapeutics 7: 62-72 for reviews). Among the considerations for achieving therapeutic efficacy by such live attenuated bacteria delivering therapeutics is the form of the therapeutic agent, which may consist of protein, carbohydrate, DNA or RNA-based therapeutics see, e.g., U.S. Pat. Nos. 7,452,531, 7,354,592, 6,962,696, 6,923,972, 6,863,894, 6,685,935, 6,475,482, 6,447,784, 6,190,657, 6,080,849 and US Pub. 2003/0059400, each of which is expressly incorporated herein by reference. Similar hurdles also exist for therapeutic vectors secreting one or more anti-infective proteins or immunomodulatory cytokines such as IL-10 (Steidler and Rottiers, 2006, "Annals of the New York Academy of Sciences 1072:176-186; Neirynck and Steidler 2006, Biotechnology & Genetic Engineering Reviews 22: 253-66; Steidler 2005," Expert opinion on drug delivery 2:737-46).

Use of protein toxins for treatment of various disorders including inflammation, autoimmunity, neurological disorders and cancer has long-suffered from off-target toxicity. Some toxins have a natural degree of specificity for their target, such as botulinum toxin which is specific for neurons and is currently marketed as the product known as Botox® (onabotulinumtoxinA). Artificial toxin specificity has been achieved by attachment of a specific antibodies or peptide ligands (e.g., *Pseudomonas* endotoxin A (PE-ToxA) antibody conjugate, known as an immunotoxin). Based upon the binding specificity of the attached antibody moiety for a specific target, enhanced specificity of the target is achieved. Other toxins have been engineered to achieve specificity based upon their sight of activation. For example, aerolysin requires proteolytic activation to become cytotoxic. Substitution of the natural protease cleavage site for a tumor-specific protease cleavage site (e.g., that of the PSA protease or urokinase) results in a toxin selectively activated within tumors. However, in both these types of engineered toxins, off-target toxicity can occur. In the case of the *Pseudomonas* immunotoxin, several dose-limiting toxicities have been identified. Vascular leakage syndrome (VLS) is associated with hypoalbuminemia, edema, weight gain, hypotension and occasional dyspnea, which is suggested to occur by immunotoxin-mediated endothelial cell injury (Baluna et al., 2000, Exp. Cell Res. 258: 417-424), resulting in a dose-limiting toxicity. Renal injury has occurred in some patients treated with immunotoxins, which may be due to microaggregates of the immunotoxin (Frankel et al., 2001, Blood 98: 722a). Liver damage from immunotoxins is a frequent occurrence that is believed to be multifactorial (Frankel, 2002, Clinical Cancer Research 8: 942-944). To date, antibodies with proteinaceous toxins have limited success clinically.

Protease inhibitors are known as drugs for treatment of diseases where proteases play a pivotal role (Turk 2006, Targeting proteases: successes, failures and future prospects. Nature Reviews Drug Discovery 5: 785-799; Motta et al., 2012; Food-grade bacteria expressing elafin protect against inflammation and restore colon homeostasis, Science Translational Medicine 4: 158 158ra144; Vergnolle et al. WO 2011/086172 Recombinant probiotic bacteria for the prevention and treatment of inflammatory bowel disease (IBD) and irritable bowel syndrome (IBS); Edwards et al., (eds) 2008; Vergnolle et al., US Patent Application 20130344033 Recombinant Probiotic Bacteria For The Prevention And Treatment Of Inflammatory Bowel Disease (IBD) And Irritable Bowel Syndrome (IBS); Edwards et al., (eds) 2009, The Cancer Degradome: Proteases and Cancer Biology, Springer; Rawlings et al., 2010, MEROPS: The Peptidase Database, Nucleic Acids Res. 2010 (Database issue): D227-33, the entirety merops•sanger•ac•uk/inhibitors/ which is expressly incorporated herein by reference; and Bermudes U.S. Pat. No. 8,241,623 Protease sensitivity expression system, and Bermudes U.S. Pat. Nos. 8,524,220 and 8,623,350 Protease inhibitor: protease sensitivity expression system compositions and methods improving the therapeutic activity and specificity of proteins delivered by bacteria), each of which is expressly incorporated herein by reference in its entirety.

Topical medications are applied to surfaces of the body including skin and mucous membranes, usually in the form of solutions, lotions, creams, ointments, gels, pastes, foams, aerosol foams or sprays, powders, solids and transdermal patches. According to DermNet NZ (dermnetnz-org/treatments/topical-formulations•html) solutions can be defined as 'water or alcoholic or solvent lotion containing a dissolved powder', lotions can be defined as 'usually considered thicker than a solution and more likely to contain oil as well as water or alcohol; a shake lotion separates into parts with time so needs to be shaken into suspension before use', creams can be defined as 'thicker than a lotion, maintaining its shape, e.g., 50/50 emulsion of oil and water; requires preservative to extend shelf life; often moisturizing', ointments can be defined as 'semi-solid, water-free or nearly water-free (80% oil); greasy, sticky, emollient, protective, occlusive; no need for preservative so contact allergy is rare; may include hydrocarbon (paraffin), wool fat, beeswax, macrogols, emulsifying wax, cetrimide or vegetable oil (olive oil, arachis oil, coconut oil)', gels can be defined as 'aqueous or alcoholic monophasic semisolid emulsion, often based on cellulose and liquefies upon contact with skin; often includes preservatives and fragrances', pastes can be defined as 'concentrated suspension of oil, water and powder', aerosol foam or sprays are defined as 'solution with pressurized propellant', powders are defined as 'solid e.g. talc (a mineral) or corn starch (vegetable)', solids are defined as "e.g., antiperspirant stick; may melt on reaching body temperature e.g. suppositories', transdermal patches can be defined as 'drug delivery systems that allows precise dosing: includes an adhesive'. The most common topical mediations are epicutaneous and are applied directly to the skin. Topical medications also included inhalational treatments such as those for asthma. Topical medications further includes those applied to a variety of other tissues, including ear drops, eye drops and various mouthwashes, and toothpastes. The topical formulations may be further modified to contain reducing agents such as methionine, glutathione, hydroquinone, vitamin C, phytic acid that reduce oxygen concentration.

Use of, compositions and formulations for topically applied bacteria have been suggested by several authors (Dondi and Malfa WO2006013441 Use of probiotic bacteria for the preparation of topical compositions for skin protection; Klapper and Malkin, WO2013067185 Probiotic stick formulation for skin maintenance and methods of use; Putaala et al., WO2012150269 Probiotic bacteria for the topical treatment of skin disorders; Ford U.S. Pat. No. 5,466,463 (WO 96/38159) Micro-encapsulated lactobacilli for medical applications; Ebinger WO2012104025 Balneotherapeutic lipid-containing probiotic preparations and their applications; Farmer JP2009269922 topical use of probiotic *Bacillus* spore for preventing or controlling microbe infection; each of which is expressly incorporated in their entirety herein) however, none have suggested human microbiome bacteria secreting protease inhibitors, alone or in combination with bacteriocins or other anti-inflammatory agents. The topical formulations containing the microorganism may be further modified to contain reducing agents such as methionine, glutathione, hydroquinone, vitamin C, phytic acid that reduce oxygen concentration, especially for microaerophilic and aneraerobic microorganisms.

There are several protease inhibitors known in bacteria, but only a few of them are known to be secreted, and otherwise they reside either within the cytoplasm or the periplasm. Known bacterial protease inhibitors include ecotin from *E. coli* (Eggers et al., 2004, The periplasmic serine protease inhibitor ecotin protects bacteria against neutrophil elastase, Biochem J. 379: 107-118), the gene product of the inh gene in *Erwinia chrysanthemi* (Letoffe and Wandersman, 1989 Characterization of a protein inhibitor of extracellular proteases produced by *Erwinia chrysanthemi*, Molecular Microbiol 3: 79-86), a protease inhibitor from *Prevotella* (Grenier 1994, Characteristics of a protease inhibitor produced by *Prevotella intermedia* FEMS Microbiol Lett 119: 13-18), *Streptomyces* subtilisin inhibitor (SSI) (Taguchi et al., 1990, Comparison of secretory expression in *Escherichia coli* and *Streptomyces* of *Streptomyces* subtilisin inhibitor (SSI) gene, Biochim Biophys Acta 1049: 278-285) and the *Bacillus* BbrPI (Shiga et al., 1991, Characterization of an extracellular protease inhibitor of *Bacillus brevis* HPD31 and nucleotide sequence of the corresponding gene, Appl. Environ. Microbiol. 58: 525-531). However, their functions remain largely unknown (Kantyka et al., 2010, Prokaryote-derived protein inhibitors of peptidases: A sketchy occurrence and mostly unknown function, Biochimie 92: 1644-1656). To date, no human microbiome protease inhibitor has been used as a therapeutic for inflammatory diseases of the skin or gut nor has it been suggested human microbiome bacteria expressing protease inhibitors would function in a therapeutic capacity as the presence of secreted protease inhibitors of the human microbiome is essentially unknown.

Proteases may be classified by several different systems, for example, into six groups based on their catalytic domain: serine proteases, threonine proteases, cysteine proteases, aspartate proteases, metalloproteases and glutamic acid proteases. Alternatively, proteases may be classified by the optimal pH in which they are active: acid proteases, neutral proteases, and basic proteases (or alkaline proteases). Serine proteases can be further subdivided into 1) trypsin-like enzymes which cleave C-terminal Arg and Lys, 2) chymotrypsin like enzymes that cleave the carboxyl side ($P_1$ position) of aromatic or large hydrophilic amino acids (tyrosine, tryptophan and phenylalanine) and 3) elastase-like enzymes that cleave the carboxyl side of small or medium size non-polar amino acids. Proteases may contribute to inflammation of the skin (Ovaere et al., 2009, The emerging roles of serine protease cascades in the epidermis. Trends Biochem Sci 34(9):453-63. doi: 10.1016/ j.tibs.2009.08.001), but it has not been suggested that bacteria expressing protease inhibitors counter balance proteases in order to maintain the normal healthy state of humans, including their skin and mucous membranes or that purified bacterial protease inhibitors would be particularly effective in treating inflammatory diseases.

The presence and possible roles of bacterial protease inhibitors from resident human microbiota has not been suggested nor has it been suggested for its potential to equalize either endogenous host proteases such as chymase, calpain, furin, kallikreins, matripase, caspases. Cathepsins, TACE, ADAM-8, ADAM-15, ADAM-17, or neutrophil serine protease nor the proteases secreted by other members of the human microbiota such as *Propionibacterium acnes, Propionibacterium acnes, Pseudomonas aeruginosa, Staphylococcus caprae, Staphylococcus aureus Staphylococcus epidermidis, Streptococcus pyogenes, Candida albicans, Proteus* sp., *Bacillus* sp., *Clostridium* sp., *Serratia* sp., *Campylobacter, Streptomyces* sp., *Porphromonas gingivalis*, or others. Among these organisms, serine proteases, cysteine proteases and metalloproteases are the most common. Protease inhibitors such as LEKTI, elafin, SLPI, SERPINs, and cystatins are thought to counter balances the activities of proteases in order to regulate their activity and maintain the integrity and protective barrier function of the skin (Meyer-Hoffert 2009 Arch Immunol Ther Exp (Warsz). 2009 September-October; 57(5):345-54. doi: 10.1007/s00005-009-0045-6. Epub 2009 Aug. 18, Reddish, scaly, and itchy: how proteases and their inhibitors contribute to inflammatory skin diseases), with inflammatory skin diseases resulting from an imbalance of inhibitors with their proteases, resulting in excessive proteases causing inflammation. And although bacterial proteases are recognized to contribute to inflammation in diseases such as cystic fibrosis (e.g., Quinn et al., Open Respir Med J. 2010; 4: 20-31) the potential for endogenous bacterial protease inhibitors has not been considered as contributing to the normal or non-inflammatory state, nor have microbiome organisms expressing protease inhibitors been considered as a counterbalance, or suggested to be modified for utilization as probiotics or genetically modified probiotics.

The protease chymase which is also known as mast cell protease I, mast cell serine proteinase, skin chymotryptic proteinase or skeletal muscle protease, is a chymotrypsin-like serine proteinase. It is primarily present in mast cell secretory granules. Chymase hydrolyzes proteins at their C-terminus after aromatic amino acids such as Trp, Tyr, or Phe. The primary target of chymase is angiotensin I, which generates angiotensin II by cleavage of angiotensin I, in the final step of the renin-angiotensin system. It is well known that angiotensin II is pivitol in hypertension as well as other pathophysiological conditions including glomerulosclerosis, atherosclerosis, cardiac hypertrophy and heart failure. Chymase also promotes mast cell degranulation thereby contributing to atopic or allergic inflammation of the skin.

Furin is an endogenous protease involved in pathological processes such as inflammation (Bassi et al., 2012, The role of proprotein convertases in animal models of skin carcinogenesis, Colloquium Series on Protein Activation and Cancer, Vol. 1: 1-60 doi: 10.4199/ C00060ED1V01Y201206PAC001). Furin is a subtilisin-like calcium-dependent serine endoprotease and is also classified as a PACE (Paired basic Amino acid Cleaving Enzyme) and is known as PACE-4.

Caspase-1 (Casp-1) is a protease that is known to process the pro-inflammatory cytokines interleukin-1β (IL-1β) and IL-18 to their active forms that participate in inflammation.

The cell-surface protease TACE (tumor-necrosis-factor-a-converting enzyme; Peschon et al. 1998, An essential role for ectodomain shedding in mammalian development, Science 282: 1281-1284; Chalaris et al., 2010, Critical role of the disintegrin metalloprotease ADAM17 for intestinal inflammation and regeneration in mice, J. Exp. Med. 208: 1617-1624) which is also known as ADAM (A Disintegrin And Metalloprotease) metallopeptidase domain 17 (ADAM17), which is a member of the ADAM family of metalloproteases and disintegrins.

Other ADAM family members are also known to be inflammatory. ADAM15 is an inflammatory enzyme (Charrier-Hisamuddin et al., 2008, ADAM-15: a metalloprotease that mediates inflammation, FASEB J 22: 641-653) as well as ADAM-8 which stimulates airway inflammation (Paulissen et al., 2011, ADAM-8, a metalloproteinase, drives acute allergen-induced airway inflammation, Eur. J. Immunol. 41: 380-391).

Kallikrein-related proteases (KLKs) are trypsin- and chymotrypsin-like serine proteases. KLK14 can represent up to 50% of the trypsin-like serine protease activity of skin and contributes to desquamation (Meyer-Hoffert 2009).

Calpain is a calcium dependent cysteine protease associated with transmigration of leukocytes that cause inflammation in pulmonary airways (Prince, WO2009145956, Uses of Calpain Inhibitors to Inhibit Inflammation).

Neutrophil serine proteases, also known as human leukocyte elastases (HLE) are present at the surface of psoriasis lesion and contribute to inflammation (Ulf Meyer-Hoffert, 2012, Epidermal Serine Proteases and Their Inhibitors in Atopic Dermatitis, Atopic Dermatitis—Disease Etiology and Clinical Management, Dr. Jorge Esparza-Gordillo (Ed.), ISBN: 978-953-51-0110-9).

Microbiome inhibitors of these proteases have not been previously described, nor have methods to derive probiotic or genetically engineered probiotic strains been developed, nor have purified microbiome protease inhibitors been developed for use in the treatment of inflammatory diseases.

3. OBJECTS OF THE INVENTION

The present invention provides, according to one embodiment, methods for elucidating one or more protease inhibitors produced by one or more bacteria or fungi of the human microbiome associated with normal health that have a therapeutic effect against inflammatory diseases of the skin, gut or mucosal surfaces of a mammal. The protease inhibitor may also serve to protect a microbiome or probiotic bacterium from elimination by phagocytes such as neutrophils. Such bacteria may be underrepresented, absent or mutated in individuals that exhibit symptoms of the disease state. Identification, purification and therapeutic use of the protease inhibitor as a purified compound, peptide or protein are also described. The invention also provides live bacteria for use as oral or topical probiotics that express therapeutic protease inhibitors alone or in combination with other protease inhibitors (as discussed above), or in combinations with bacteriocins (bacterially produced antibacterial agents that inhibit other strains of bacteria but not the host strain that produces them), such as lactococcins, microcins or colicins (Riley and Chavan 2006, Bacteriocins: Ecology and Evolution, Springer; de Vuyst and Vandamme 2012, Bacteriocins of lactic acid bacteria; Microbiology, genetics and applications, Blackie Academic & Professional Press) in order to facilitate colonization of a region which is facilitated by the presence of a bacteriocin that eliminates some or all of the bacteria present in that location.

Live attenuated bacterial strains that co-express protease inhibitors together with one or more bacteriocins have not been previously suggested as being beneficial. The combination of bacterial protease inhibitors, bacteriocins and antibodies is also described.

The bacterial delivery vector may also be attenuated, non-pathogenic, low pathogenic (including wild type), or a probiotic bacterium. The bacteria are introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically (solutions, lotions, creams, ointments, gels, pastes, foams, aerosol foams or sprays, powders, solids and transdermal patches), intathecally (intrathecal), by inhaler or nasal spray) or to the mucosal system through oral, nasal, pulmonary intravessically, enema or suppository administration. The terms "oral", "enteral", "enterally", "orally", "non-parenteral", "non-parenterally", and the like, refer to administration of a compound or composition to an individual by a route or mode along the alimentary canal. Examples of "oral" routes of administration include, without limitation, swallowing liquid or solid forms by the mouth, administration of a composition through a nasojejunal or gastrostomy tube, intraduodenal administration of a composition, and rectal administration, e.g., using suppositories that release a live bacterial strain described herein to the lower intestinal tract of the alimentary canal. Upon administration, the bacteria are able to undergo limited or unlimited replication, express, surface display, secrete and/or release the protease inhibitors with anti-inflammatory effects, and thereby provide a therapeutic benefit by reducing or eliminating the anti-inflammatory disease.

When administering self-replicating organisms, the minimum dose approximates a single in vivo replication competent organism ($1\times10^0$) or minimum infectious dose, which itself is approximated by an in vitro determined colony forming unit (c.f.u.). However, higher doses are preferred, in order to permit prompt initiation of therapeutic effect and avoid host immune response suppression of the organisms before they reach full therapeutic potential, and therefore doses as high as $1\times10^{12}$ may be used. In some cases, replication incompetent organisms may be used, e.g., where the organisms remain competent to produce the biologically active products as discussed herein, in which case a dose may be, for example, in the range $10^8$ to $10^{10}$ organisms. It is a particular benefit that the probiotic bacteria provided are naturally tolerated by the animal host. For example, it is preferred that the probiotic bacteria produce a small immunostimulatory effect; if the effect is too low, the probiotic bacteria could become pathogenic (an "infection"), at least in some hosts. If the immunostimulatory effect is too large, two adverse effects are seen: the immunostimulation itself may lead to erythema or other immune mediated effect, and second, the persistence of the bacteria may be adversely effected and the therapeutic effect of the bacteria product attenuated.

The present invention further encompasses the co-expression by a bacterial expression system, or a combination of bacterial expression systems, of one or more protease inhibitors, which may be alone or together with one or more bacteriocins, or an additional anti-inflammatory agent, whereby the protease inhibitors inhibit antigen processing of endosomal and/or proteosomal proteases, thereby reducing or essentially eliminating immune responses to the bacterial vector and/or the inflammatory disease.

The present invention further encompasses the co-expression by a bacterial expression system, or a combination of bacterial expression systems, of a peptide that modulates tight junctions utilizing the small non-toxic Zonula occuluta toxin (Zot) peptide AT10002 (Song et al. 2008, Enhanced nasal absorption of hydrophilic markers after dosing with AT1002, a tight junction modulator, Eur J Pharm Biopharm 69: 231-237) which is the active Zot domain (aa 288-293) with the amino acid sequence: FCIGRL SEQ ID:001.

The present invention also encompasses generation of Gram positive bacteria such as *Lactococcus lactis, Lactococcus casei, Lactobacillus acidophilus, Streptococcus salivarus, Staphylococcus epidermidis, Propionibacterium acnes, Propionibacterium* sp. adapted to secrete protease inhibitors. The protease inhibitors are produced by attenuated, probiotic or commensal bacteria that are able to reside within the disease site such as the skin, gut, tumor or parasite infected area without themselves causing disease, thus releasing the protease inhibitors in direct proximity to disease targets.

The present invention provides, according to one aspect, for example, and without limitation, live bacterial compositions that are genetically engineered to express one or more protease inhibitors combined with plasmids, phagemids, phage or viroids capable of delivering protein and antibody therapeutics for suppressing inflammatory diseases of the skin, gut, vagina nasopharyngeal region and bladder.

The present invention also encompasses bacteria suitable for administration to humans and other mammals or birds or wild animals, pets and livestock, that either expressed, released, surface display or secrete proteins including protease inhibitors in combination with plasmids, as either expressed, released, surface displayed or secreted by bacteria that are able to deliver peptides, antibodies, DNA or RNA based therapeutics resulting in anti-inflammation as is involved in a number of disease pathologies.

In one embodiment, the bacteria secrete protease inhibitors in combination with anti-inflammatory proteins (Castellani et al., 2007, Anti-chemokine therapy for inflammatory diseases, Int J Immunopathol Pharmacol, 20:447-453; Cianciarullo and Ceccon 2010, Pro-inflammatory and anti-inflammatory cytokines: Homeostasis and/or an imbalance in neonatal sepsis, VDM Publishers, 104 pages; Dinarello 2002, Pro-inflammatory and anti-inflammatory cytokines in rheumatoid arthritis: a primer for clinicians, 3rd Edition, Amgen, 351 pages) such as inhibitors or antibodies against phosphodiesterase 4, IL4, IL-10, IL-1Ra, IL-17, IL-23, lactoceptin (von Schillde et al., 2012 Lactocepin secreted by *Lactobacillus* exerts anti-inflammatory effects by selectively degrading pro-inflammatory chemokines Cell Host Microbe. 11:387-96) or the tripeptide FEG (Phe-Glu-Gly; FEG) and/or submandibular gland peptide-T (TDIFEGG SEQ ID:002) or adapting the bacteria to secret the *Yersinia* protein LcrV which thereby induces anti-inflammatory IL10. Virally delivered anti-inflammatory proteins adapted to bacterial delivery by addition of a bacterial secretion signal are also encompassed (Zheng et al., 2012, Virus derived anti-inflammatory proteins: potential therapeutics for cancer, Trends in Molecular Medicine 18: 304-310).

In another embodiment, the bacteria secrete protease inhibitors co-expressed with surface display antibodies against inflammatory agents, such as antibodies against tumor necrosis factor alpha (TNF-alpha) and thereby inhibit TNF-alpha mediated inflammation, or antibodies against TNF-beta, thereby inhibiting TNF-beta mediated inflammation, or antibodies against IL1b thereby inhibiting IL1b mediated inflammation, or antibodies to GM-CSF (e.g., the antigen binding region of the antibody MOR103), thereby inhibiting GM-CSF mediated inflammation, or antibodies against IL12 (e.g., the antigen binding region of the antibody ABT-874), thereby inhibiting IL12 mediated inflammation, or an antibody against IL13 (e.g., the antigen binding region of the antibody CAT354), thereby inhibiting IL13 mediated inflammation, or an antibody against B-lys (e.g., the antigen binding region of lymphostat-BTM), thereby inhibiting B-lys mediated inflammation, or an antibody against IL-17 or IL-23, thereby inhibiting inflammation, or combinations thereof.

In another embodiment, the protease inhibitor is co-expressed with a phage that delivers one or more miRNA that is anti-inflammatory.

In another embodiment, the protease inhibitor is co-expressed with a phage that delivers one or more antisense RNA to an inflammatory associated miRNA, thereby inhibiting that miRNA and reducing inflammation.

In another embodiment the protease inhibitor is co-expressed with a phage that delivers one or more siRNA for an inflammatory molecule such as TNF-alpha and/or TNF-beta, thereby reducing or effectively eliminating inflammation.

Expression of antibody deactivating proteins are also encompassed by embodiments of the present invention. The antibody deactivating proteins serve two purposes, one being to prevent the elimination of the bacterial vector, which, while expressing protease inhibitors and various peptides, plasmids, phage, phagemids and/or viroids, may generate an immune response to these heterologous peptides which could results in generating an immune response that would eliminate the bacterial vector. The antibody deactivating protein delays the elimination of the bacteria, resulting in a prolonged delivery of the therapeutic components. Antibody deactivating proteins include the IgA protease from Nisseria (when it is not being used as a fusion protein for secretion or surface display, used primarily in Gram negative bacteria), the IgA protease of *Haemophilus*, IdeS (an IgG protease), the IgG protease of *Pseudomonas* (pseudolysin), or *Proteus mirabilis* (mirabilysin), *Treponema* (trepolisin) *Staphylococcus* (glutamyl endopeptidase I GluV8), or for Gram positive bacteria, the IgA protease of *Streptococcus pneumonia* EndoS proteases from *Staphalococcus*, the *Staphalococcus* antibody-binding protein A, and *Shistosoma* IgE proteases. The expression of the antibody deactivating proteins may be under transcriptional control by bacterial promoters that are inducible or constitutive. The antibody deactivating proteins may also contribute to reduced inflammation, since antibodies have the ability to serve as ligands for inflammatory cells such as macrophages, neutrophils, NK cells, dendridic cells and mast cells, their localized reduction by the therapeutic bacteria results in an additional suppression of inflammation. Expression of other immune evasive proteins such as AurA, YopJ and VacA are also encompassed (Coombes, et al., 2004, Evasive maneuvers by secreted bacterial proteins to avoid innate immune responses, Curr Biol 14:R856-R867; Findlay and McFadden 2006, Anti-Immunology: Evasion of the Host Immune System by Bacterial and Viral Pathogens, Cell 124, 767-782), expressly incorporated by reference herein in its entirety.

The present invention provides, according to various embodiments, live attenuated, probiotic or commensal bacterial strains such as *Propionibacterium acnes, Propionibacterium* sp., *Corynebacterium* sp., *E. coli, Streptococcus salivarius, Lactococcus* sp, or *Lactobacillus* sp. strains that express, release, surface display or secret one or more therapeutic proteins such as a protease inhibitor alone or together with plasmids, phage, phagemids or viroids that are able to deliver peptides and antibodies-based therapeutics that deliver protease inhibitors that reduce symptoms inflammatory diseases.

In one embodiment, the live attenuated, probiotic or commensal bacterial strains such as *Propionibacterium acnes, Propionibacterium* sp., *Corynebacterium* sp., *E. coli, Streptococcus salivarius, Lactococcus* sp, or *Lactobacillus* sp strains express, release, surface display or secret one or more protease inhibitors interfering with inflammation.

A preferred composition will contain, for example, a sufficient amount of live bacteria to produce a therapeutic response in the patient. Accordingly, the attenuated bacterial strains described herein are both safe and useful as live bacterial vectors that can be topically, orally or systemically administered to an individual to provide therapeutic benefit against inflammation.

Although not wishing to be bound by any particular mechanism, an example of an effective anti-inflammatory response in humans and other mammals or birds or wild animals, pets and livestock, by administration of microbiome, genetically engineered and/or attenuated strains of bacteria as described herein may be due to the ability of such strains to persist in the skin or mucosal surfaces such as in the intestine, and continuously inhibit factors at those targets, having an anti-inflammatory effect. Bacterial strains useful in accordance with a preferred aspect of the invention may carry the ability to produce a therapeutic molecule from an exogenous plasmid, the endogenous virulence plasmid, or chromosomally integrated cassette that encodes and directs expression of one or more therapeutic molecules.

Preferably, the bacteria display site-specific colonization of the tissue, and does not tend to colonize broad range of tissues. This permits specific therapies, with reduce risk of activity outside the intended target tissue. For example, a powerful anti-inflammatory effect may be undesirable outside the tissue of administration.

The serovars of *Salmonella enterica* that may be used as the attenuated bacterium of the live compositions described in accordance with various embodiments herein include, without limitation, *Propionibacterium acnes, Salmonella enterica* serovar *Typhimurium* ("*S. typhimurium*"), *Salmonella montevideo, Salmonella enterica* serovar *Typhi* ("*S. typhi*"), *Salmonella enterica* serovar *Paratyphi* B ("*S. paratyphi* B"), *Salmonella enterica* serovar *Paratyphi* C ("*S. paratyphi* C"), *Salmonella enterica* serovar *Hadar* ("*S. hadar*"), *Salmonella enterica* serovar *Enteriditis* ("*S. enteriditis*"), *Salmonella enterica* serovar *Kentucky* ("*S. kentucky*"), *Salmonella enterica* serovar *Infantis* ("*S. infantis*"), *Salmonella enterica* serovar *Pullorum* ("*S. pullorum*"), *Salmonella enterica* serovar *Gallinarum* ("*S. gallinarum*"), *Salmonella enterica* serovar *Muenchen* ("*S. muenchen*"), *Salmonella enterica* serovar *Anatum* ("*S. anatum*"), *Salmonella enterica* serovar *Dublin* ("*S. dublin*"), *Salmonella enterica* serovar *Derby* ("*S. derby*"), *Salmonella enterica* serovar *Choleraesuis* var. *kunzendorf* ("*S. cholerae kunzendorf*"), and *Salmonella enterica* serovar *minnesota* (*S. min-*

*nesota*). A preferred serotype for the treatment of bone marrow related diseases is *S. dublin*.

By way of example, live bacteria in accordance with aspects of the invention include known strains of *S. enterica* serovar *Typhimurium* (*S. typhimurium*) and *S. enterica* serovar *Typhi* (*S. typhi*) which are further modified as provided by various embodiments of the invention. Such Strains include Ty21a, CMV906, CMV908, CMV906-htr, CMV908-htr, Ty800, aroA-/serC-, holavax, M01ZH09, VNP20009. See also, U.S. Pat. No. 6,548,287, and EP 0,973,911, each of which expressly incorporated herein by reference. These strains contain defined mutations within specific serotypes of bacteria. The invention also includes the use of these same mutational combinations contained within alternate serotypes or strains in order to avoid immune reactions which may occur in subsequent administrations. In a preferred embodiment, *S. Typhimurium, S. montevideo*, and *S. typhi* which have non-overlapping 0-antigen presentation (e.g., *S. typhimurium* is 0-1, 4, 5, 12 and *S. typhi* is Vi, *S. montevideo* is 0-6, 7) may be used. Thus, for example, *S. typhimurium* is a suitable serotype for a first injection and another serotype such as *S. typhi* or *S. montevideo* are used for a second injection and third injections Likewise, the flagellar antigens are also selected for non-overlapping antigenicity between different injections. The flagellar antigen may be H1 or H2 or no flagellar antigen, which, when combined with the three different O-antigen serotypes, provides three completely different antigenic profiles. Methods for deriving heterologous O-antigens have been described by Favre et al., WO/1997/014782, and Roland WO/2000/004919, each of which is expressly incorporated herein by reference.

Novel strains are also encompassed that are, for example, attenuated in virulence by mutations in a variety of metabolic and structural genes. The invention therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is the Suwwan deletion (Murray et al., Journal of Bacteriology, 2004) or combinations with other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, pur, purA, purB, purl, purF, zwf, aroA, aroB, aroC, aroD, serC, gua, cadA, rfc, rjb, rfa, ompR, msbB and combinations thereof. Strains of *Salmonella* deleted in stn are particularly preferred.

The invention also encompasses attenuated gram-positive bacteria. For example, *Propionibacterium* sp., *Corynebacterium* sp., *E. coli, Streptococcus salivarius, Lactococcus* sp, or *Lactobacillus* sp, *Staphylococcus epidermidis*, group B *Streptococcus* including *S. agalaciae*, and *Listeria* species including *L. monocytogenes* may be employed. It is known to those skilled in the art that variations in molecular biology techniques such as use of gram-positive origins of replication, gram-positive signal sequences and gram-positive promoters and filamentous phage (e.g., phage B5; Chopin et al., 2002 J. Bacteriol. 184: 2030-2033 described further below) may be employed and substituted as needed. Other bacterial strains may also be encompassed, including non-pathogenic bacteria of the gut skin (such as *Staphylococcus epidermidis, Propionibacteria* sp.) and other body locations known as the human microbiome (Grice et al., Topographical and temporal diversity of the human skin microbiome, Science 324: 1190-1192; A framework for human microbiome research; The Human Microbiome Project Consortium, 14 Jun. 2012 Nature 486, 215-221; Spor et al., 2011, Unraveling the effects of the environment and host genotype on the gut microbiome, Nature Reviews Microbiology 9: 279-290) such as *E. coli* strains, *Bacteriodies* sp., *Bifidobacterium* sp. and *Bacillus* sp., attenuated pathogenic strains of *E. coli* including enteropathogenic and uropathogenic isolates, *Enterococcus* sp. and *Serratia* sp. as well as attenuated *Neisseria* sp., *Shigella* sp., *Staphylococcus* sp., *Staphylococcus carnosis, Yersinia* sp., *Streptococcus* sp. and *Listeria* sp. Bacteria of low pathogenic potential to humans and other mammals or birds or wild animals, pets and livestock, such as insect pathogenic *Xenorhabdus* sp., *Photorhabdus* sp. and human wound *Photorhabdus* (*Xenorhabdus*) are also encompassed. Probiotic strains of bacteria are also encompassed, including *Lactobacillus* sp. (e.g., *Lactobacillus acidophilus, Lactobacillus salivarius*) *Lactococcus* sp., (e.g., *Lactococcus lactis, Lactococcus casei*) *Leuconostoc* sp., *Pediococcus* sp., *Streptococcus* sp. (e.g., *S. salivariu, S. thermophilus*), *Bacillus* sp., *Bifidobacterium* sp., *Bacteroides* sp., and *Escherichia coli* such as the 1917 Nissel strain. It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 114331-4336) may be used and substituted as needed. The bacteria may be further modified to be internalized into the host cell (Guimaraes et al., 2006, Use of Native Lactococci as Vehicles for Delivery of DNA into Mammalian Epithelial Cells, Appl Environ Microbiol. 2006 November; 72(11): 7091-7097: Innocentin et al., 2009, *Lactococcus lactis* Expressing either *Staphylococcus aureus* Fibronectin-Binding Protein A or *Listeria monocytogenes* Internalin A Can Efficiently Internalize and Deliver DNA in Human Epithelial Cells Appl Environ Microbiol. 2009 July; 75(14): 4870-4878).

It is therefore an object to provide a bacterium expressing a protease inhibitor and optionally capable of delivering a bacteriocin or an antibody, adapted for treatment of an inflammatory disease in an animal.

The target tissue may be, for example, skin having psoriasis, skin having atopic dermatitis, skin having acne, gut tissue having inflammatory bowel disease, or bladder tissue having in situ bladder cancer. The vector may produce, for example, therapeutic protease inhibitor, a bacteriocin and an anti-TNF-alpha.

The peptide associated with the therapeutic may comprise a peptide produced by the bacterium. The peptide may be heterologous with respect to the animal or the microorganism. The protease inhibitor may be produced by the bacterium in an inactive form and be activated by the animal. The peptide associated with the therapeutic may also comprise a peptide produced by animal host cells in response to the therapeutic.

A further object provides a system and method and a genetically engineered organism, which uses co-expression of protease inhibitors and protease sensitive therapeutic agents including phage and phagemids delivering peptides, therapeutic antibodies, DNA and RNA-based therapeutics that results in treating inflammation of a variety of disorders including psoriasis, atopic dermatitis and inflammatory bowel disease.

It is a further object to provide a method of screening microorganism from mixed populations for the production of secreted protease inhibitors, comprising: growing a mixed population of microorganisms on protease-detection media; adding a protease followed by at least one antibiotic; and detecting protease inhibition.

It is also an object to provide a pharmaceutical formulation, comprising a substantially purified protease inhibitor derived from a microorganism selected for production of protease inhibitors, in a pharmaceutically acceptable formulation.

It is a further object to provide a microorganism produced by a process comprising: growing colonies of at least one microorganism from a mixed population of microorganisms on protease-detection media; adding a protease followed by an antibiotic treatment, such that no colonies undergo additional growth in the presence of the protease on the protease detection media; detecting enhanced inhibition of the protease by colonies of the at least one microorganism; and selecting at least one colony based on the detected protease inhibition, wherein the selected at least one colony is subjected to at least one of guided evolution, mutagenesis, and genetic engineering to produce a defined change in genome, such that the selected at least one colony differs from the bacteria in the mixed population of microorganisms.

The method may further comprise selecting from the mixed population of microorganisms grown on the protease-detection media a subpopulation having enhanced production of protease inhibitors.

The method may further comprise mutating at least one microorganism from the mixed population of microorganisms to form at least one mutant. The method may further comprise selecting at least one mutant of the mixed population of microorganisms based on the detected protease inhibition. The method may further comprise selecting the microorganisms grown on the protease-detection media for enhanced production of at least one protease inhibitor.

The method may further comprise isolating at least one protease inhibitor from selected microorganisms.

The method may further comprise selecting administering at least one isolated protease inhibitor in a pharmaceutically acceptable dosage form to a human for treatment of at least one inflammation associated from a disorder selected from the group acne, psoriasis, atopic dermatitis, eczema and inflammatory bowel disease.

The protease detection media may selects for inhibition of at least one of the enzyme chymase, the enzyme calpain, the enzyme Casp-1, proteases from *Staphylococcus aureus*, and the enzyme neutrophil serine protease elastase.

The pharmaceutical formulation may provide the purified protease inhibitor in a sufficient dose and in a suitable formulation for treatment of a human having for at least one inflammation associated from a disorder selected from the group acne, psoriasis, atopic dermatitis, eczema and inflammatory bowel disease.

The microorganism may be selected from the group consisting of *Propionibaterium acnes, Pseudomonas aeruginosa, Staphylococcus aureus, Staphylococcus caprae, Staphylococcus epidermidis, Streptococcus pyogenes, Candida albicans, Proteus* sp., *Bacillus* sp., *Clostridium* sp., *Serratia* sp., *Campylobacter, Streptomyces* sp., *Porphromonas gingivalis, Lactococcus lactis, Lactococcus casei, Lactobacillus acidophilus, Streptococcus salivarus, Propionibacterium* sp, *Corynebacterium* sp., *E. coli, S. agalaciae,* and *Listeria monocytogenes.*

The target tissue may be selected from the group consisting of: skin exhibiting symptoms of psoriasis, skin exhibiting symptoms of atopic dermatitis, skin exhibiting symptoms of eczema, skin exhibiting symptoms of acne, and skin exhibiting symptoms of psoriasis.

The selected microorganism may produce a protease inhibitor that reduces inflammation of at least one of skin and mucus membranes in an animal.

The microorganism may be a probiotic bacteria which colonies at least one of human skin, human mucous membranes, and human gut substantially without causing disease in health adult humans, and which produces a protease inhibitor in situ.

The microorganism may comprise synthetic DNA.

4. BRIEF DESCRIPTION OF THE DRAWINGS

5. DETAILED DESCRIPTION OF THE INVENTION

Figure 1:
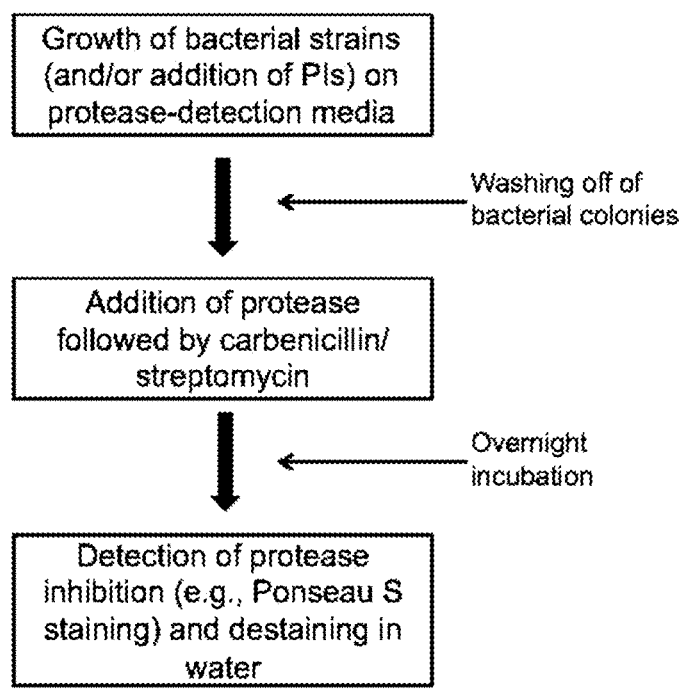
FIG. 1 shows a stepwise procedure for detecting protease inhibitors.

The present invention provides, according to one embodiment, live attenuated bacterial strains that co-express protease inhibitors together with one or more plasmids, phage, phagemids or viroids that carry peptides, antibodies, DNA or RNA based therapeutics. The plasmids, phage, phagemids, or viroids may be carried by either gram negative bacteria, wherein the phage is based on M13, or gram positive bacteria, wherein the phage is based on B5; the viroids which can be carried in either gram positive or gram negative are based on plant viroids or mammalian hepatitis D (Rocheleau L, Pelchat M (2006). "The Subviral RNA Database: a toolbox for viroids, the hepatitis delta virus and satellite RNAs research". BMC Microbiol. 6: 24. doi: 10.1186/1471-2180-6-24). The phage may be particularly effective in suppressing inflammatory responses through a combination of the effects of the protease inhibitor together with either an externally displayed anti-inflammatory peptide, an externally displayed anti-inflammatory antibody, a DNA encoded anti-inflammatory molecule or a therapeutic RNA, including miRNAs, antisense miRNAs and siRNAs. Certain modifications of the phage, phagemids or viroids may also be useful in treating certain virally infected cells, cancer or parasitic diseases such as worms.

The present invention provides, according to various embodiments, improved live attenuated therapeutic bacterial strains that express one or more therapeutic molecules. The primary characteristic of the bacteria of certain embodiments of the invention is the enhanced effect in treatment of inflammatory disease of the skin and other locations. In one embodiment, the percent increase in effect is approximately 2% to approximately 95%, approximately 2% to approximately 75%, approximately 2% to approximately 50%, approximately 2% to about 40%, approximately 2% to about 30%, approximately 2% to about 25%, approximately 2% to about 20% or about 2% to approximately 10% greater than the parental strain of bacteria without expressing one or more invasion mutations or cell wall defects under the same conditions.

For reasons of clarity, the detailed description is divided into the following subsections: mixed microorganism protease inhibitor assay, protease inhibitors, bacteriocins, antibody producing bacteria and determination of synergy.

5.1 Mixed Microorganism Protease Inhibitor Assay.

Protease inhibitor producing microbiota of the invention are novel protease inhibitors isolated from the human microbiome; methods and examples for their isolation are described herein. The assay is directed toward the identification of microorganisms secreting protease inhibitors in order for the inhibitor to be identified and facilitate its use as a purified protease inhibitor such as a topical formulation. The assay also allows identification of microorganisms secreting protease inhibitors in order for the microorganism to be used as a probiotic. The same microorganism can be phenotypically selected or genetically modified to produce a greater quantity of the protease inhibitor using methods known to those skilled in the arts. The microorganisms can also be further modified to express one or more bacteriocins and/or anti-inflammatory antibodies or peptides using methods known to those skilled in the arts.

Microbiome samples are taken using standard techniques including skin swabs and Biord Deep Cleansing Pore Strips, (Kao Brands Company, Cincinnati, Ohio) which have been used for human skin microbiome studies (e.g., Fitz-Gibbon et al., 2013 *Propionibacterium acnes* Strain Populations in the Human Skin Microbiome Associated with Acne, Journal of Investigative Dermatology 133:2152-60). Standard microbiological media described by Kreig, 1981 (Chapter 8, Enrichment and Isolation, p. 112-142 in Manual of Methods for General Bacteriology, Gerhardt et al., eds, American Society for Microbiology, Washington, D.C.) such as Mueller Hinton and chocolate agar under aerobic, microaerophilic and anaerobic conditions. These organisms can then be screened as described in Example 1.

Petri plate modifications. Typical petri plates are contain 1.5% agar in order to generate a solid support. Modified supports may consist of higher or lower agar concentrations, and/or varying concentrations of starch, silica, acrylamide, gelatin, casein, cellulose, clay, montmorillonites, or other solidifying supports.

Petri plates may be further modified with porous membranes on the surface that they allow protein diffusion and facilitate the microbial colonies to be transferred to another growth medium or to a biochemical assay while preserving their spatial organization which then allows retracing a position on a plate to a particular organism on a master plate. Porous membranes include cellulose, cellulose esters, cellophane, polyestersulfone (PES), nylon, polytetrafluoroethylene (PTFE, a.k.a. Teflon) including hydrophobic and hydrophilic forms, as well as membranes with protein binding ability that allow small molecule diffusion including polyvinylidene fluoride, or polyvinylidene difluoride (PVDF) and nitrocellulose. The purpose of these supports is that they allow transfer of the metabolically active microorganism from a type of petri plate that may not be fully compatible with the assay and allows the bacteria secrete the protease inhibitor(s) during the period the microorganism remain metabolically active.

The composition of the petri plates is matched to the protease for which the specific protease inhibitor is being screened for. For isolation of general protease inhibitors, the compositions of Table 1 may be used. Variations, such as alternate proteins as indicators, such the dye-bound protein azocoll (Chavira et al., 1984, Assaying proteases with azocoll, Anal Biochem 136: 446-450), can also be used.

TABLE 1

Classes of proteases, substrates, proteases for substrate clearance, and cognate inhibitor controls that can be used for a petri plate assay to isolate classes of protease inhibitors.

| Class of Protease | Substrate | Protease for substrate clearance | Cognate inhibitor control |
|---|---|---|---|
| Serine | Gelatin/casein | A) Trypsin, B) Thymostrypsin, C) Elastase | Aprotinin |
| Cysteine | Gelatin/casine | Papain | Leupeptin |
| Aspartic acid | Gelatin/casein | Pepsin | Pepstatin |
| Metalloprotease | Gelatin/casein | Thermolysin | α-2-macroglobulin |

The general formula outlined above in Table 1 can be further modified to screen for specific inhibitors (Table 2).

TABLE 2

Representative petri plate components for isolation of protease enzyme specific inhibitors.

| Protease Target | Substrate | Protease for substrate clearance | Cognate inhibitor control |
|---|---|---|---|
| *Propionibacterium acnes* | Gelatin/casein | Purified I proteases from *Propionibacterium acnes* (Ingram et al., 1983 *J. Appl. Bacteriol* 54: 263-271; Lee et al., 2010 *Arch Dermatol Res.* 302: 745-756) | |
| *Propionibacterium acnes* | Gelatin/casein | Purified II proteases from *Propionibacterium acnes acnes* (Ingram et al., 1983 *J. Appl. Bacteriol* 54: 263-271; Lee et al., 2010 *Arch Dermatol Res.* 302: 745-756) | |
| *Propionibacterium acnes* | Gelatin/casein | Purified III proteases from *Propionibacterium acnes acnes* (Ingram et al., 1983 *J. Appl. Bacteriol* 54: 263- | |

TABLE 2-continued

Representative petri plate components for isolation of protease enzyme specific inhibitors.

| Protease Target | Substrate | Protease for substrate clearance | Cognate inhibitor control |
|---|---|---|---|
| | | 271; Lee et al., 2010 *Arch Dermatol Res.* 302: 745-756) | |
| Chymase | Gelatin/casein N-Succinyl-Ala-Ala-Pro-Phe p-nitroanilide SEQ ID NO.: 005 (Sigma Aldrich) | Chymase | Z-Arg-Glu-Thr-Phe p (OPh)$_2$ SEQ ID NO.: 006 (MP Biomedical) |
| Calpain | Gelatin/casein Proluminescent calpain substrate, Suc-LLVY-aminoluciferin SEQ ID NO.: 007 (Promega, Madison, WI) | Calpain | Calpastatin, N-Acetyl-L-leucyl-L-leucyl-L-norleucinal (Sigma Aldrich) |
| Furin | Gelatin/Casein Boc-Arg-Val-Arg-Arg-AMC SEQ ID NO.: 008 (AMC = 7-Amino-4-methylcoumarin) (Enzo Life Science) | Furin | Furin Inhibitor I N$^2$-(Decanoyl-RVKR-CMK) SEQ ID NO.: 009 (EMD Millipore) |
| Casp-1 | Gelatin/casein YVAD-AFC SEQ ID NO.: 010 emits blue light (400 nm); upon cleavage of the substrate by caspase-1 or | Casp-1 | Caspase-1 Inhibitor VI (Z-YVAD-FMK) SEQ ID NO.: 011 (Calbiochem) |
| Neutrophil serine protease elastase inhibitor | Gelatin/Casein | Neutrophil serine protease elastase inhibitor | Elafin |
| MMP2/9 | Gelatin/casein MMP-2/MMP-9 Substrate II Ac-Pro-Leu-Gly-(2-mercapto-4-methylpentanoyl)-Leu-Gly-OEt SEQ ID NO.: 012 (Millipore EMD 444224) | MMP2/9 | MMP-2/MMP-9 Inhibitor II; CAS 193807-60-2 (Calbiochem) |

The general formulas outlined above in Tables 1 and 2 can be further modified to screen for species specific inhibitors (Table 3) against purified enzymes using published methods.

TABLE 3

Representative petri plate components for isolation of species-specific protease enzyme inhibitors for purified proteases.

| Protease producing species target | Substrate | Protease for substrate clearance | Cognate inhibitor control |
|---|---|---|---|
| *Propionibacterium acnes* | Gelatin/casein | Protease containing culture supernatant from *Propionibacterium acnes* (Ingram et al., 1983 *J. Appl. Bacteriol* 54: 263-271; Lee et al., 2010 *Arch Dermatol Res.* 302: 745-756) | |
| *Staphylococcus aureus* | Gelatin/casein | SspB Cysteine protease from *Staphylococcus aureus*. | E-64 |

TABLE 3-continued

Representative petri plate components for isolation of species-specific protease enzyme inhibitors for purified proteases.

| Protease producing species target | Substrate | Protease for substrate clearance | Cognate inhibitor control |
|---|---|---|---|
| Pseudomonas aeruginosa | Gelatin/casein | Zinc metalloprotease from Pseudomonas aeruginosa | HSCH2 (DL)CH[CH2CH(CH3)2]CO-Phe-Ala-NH2 |
| Pseudomonas aeruginosa | Gelatin/casein | Elastase Pseudomonas aeruginosa | 2-mercaptoacetyl-L-phenylalanyl-L-leucine |

The general formulas outlined above in Tables 1, 2 and 3 can be further modified to screen for inhibitors culture supernatants (Table 4). The culture supernatants can contain proteases that have not been characterized, or they may contain mixtures of proteases.

TABLE 4

Representative petri plate components for isolation of species-specific protease enzyme inhibitors.

| Protease producing species target | Substrate | Protease for substrate clearance |
|---|---|---|
| Staphylococcus aureus | Gelatin/casein | Protease containing culture supernatant of Staphylococcus aureus. |
| Staphylococcus epidermidis | Gelatin/casein | Protease containing culture supernatant of Staphylococcus epidermidis. |
| Clostridium difficile | Gelatin/casein | Protease containing culture supernatant of Clostridium difficile |
| Pseudomonas aeruginosa | Gelatin/casein | Protease containing culture supernatant of Pseudomonas aeruginosa |

Figure 5A:
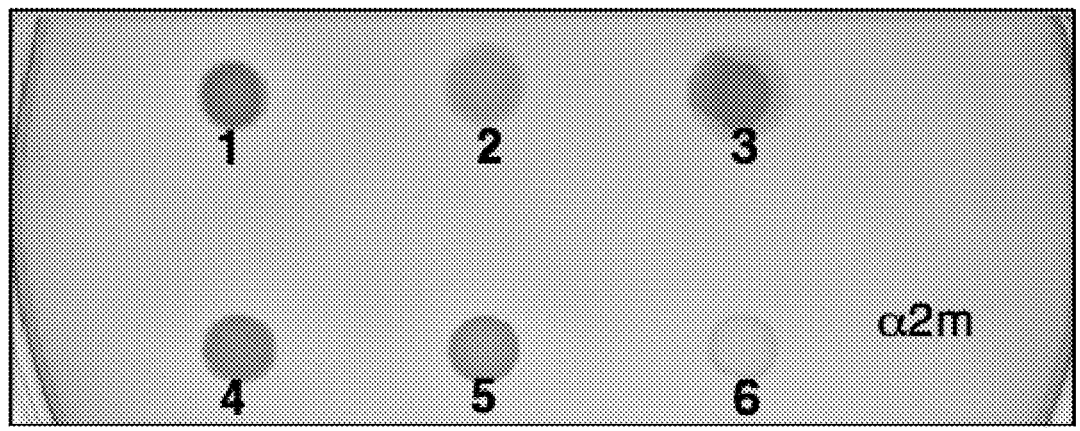
FIGS. 5A and 5B show bacterial protease inhibitor zones of protease protection.
Figure 5B:
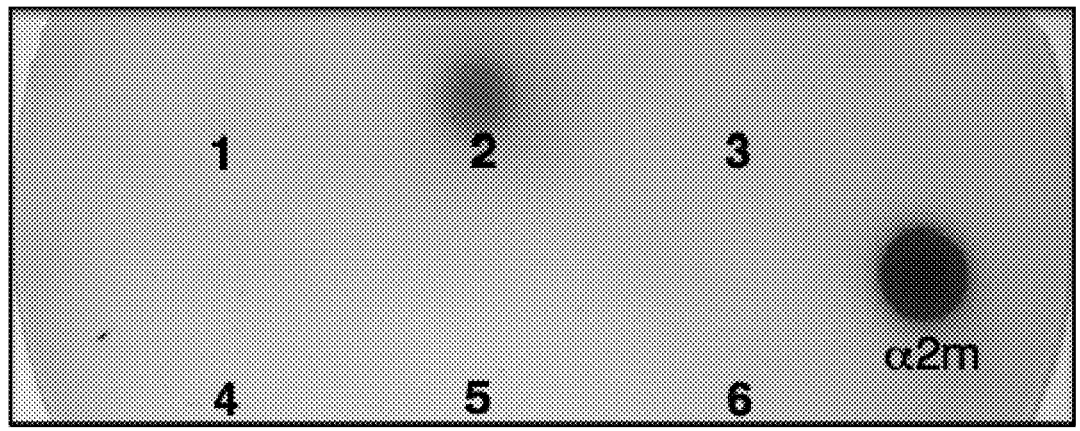

The bacteria may be further selected for enhanced protease inhibitor production. The methods described herein include a culture-based method for the isolation of microorganisms producing protease inhibitors. The production of the protease inhibitors is visualized on a petri dish (FIGS. 5A and 5B). Using methods known to those skilled in the arts which include various mutagenesis methods such as exposure to ultraviolet light, chemical mutagens such as nitrosoguanidine, or genetic methods such as transposon mutagenesis, organisms with improved production of protease inhibitors are visualized as producing more intensely staining zone of protease protection.

5.2 Protease Inhibitors.

Figure 6:
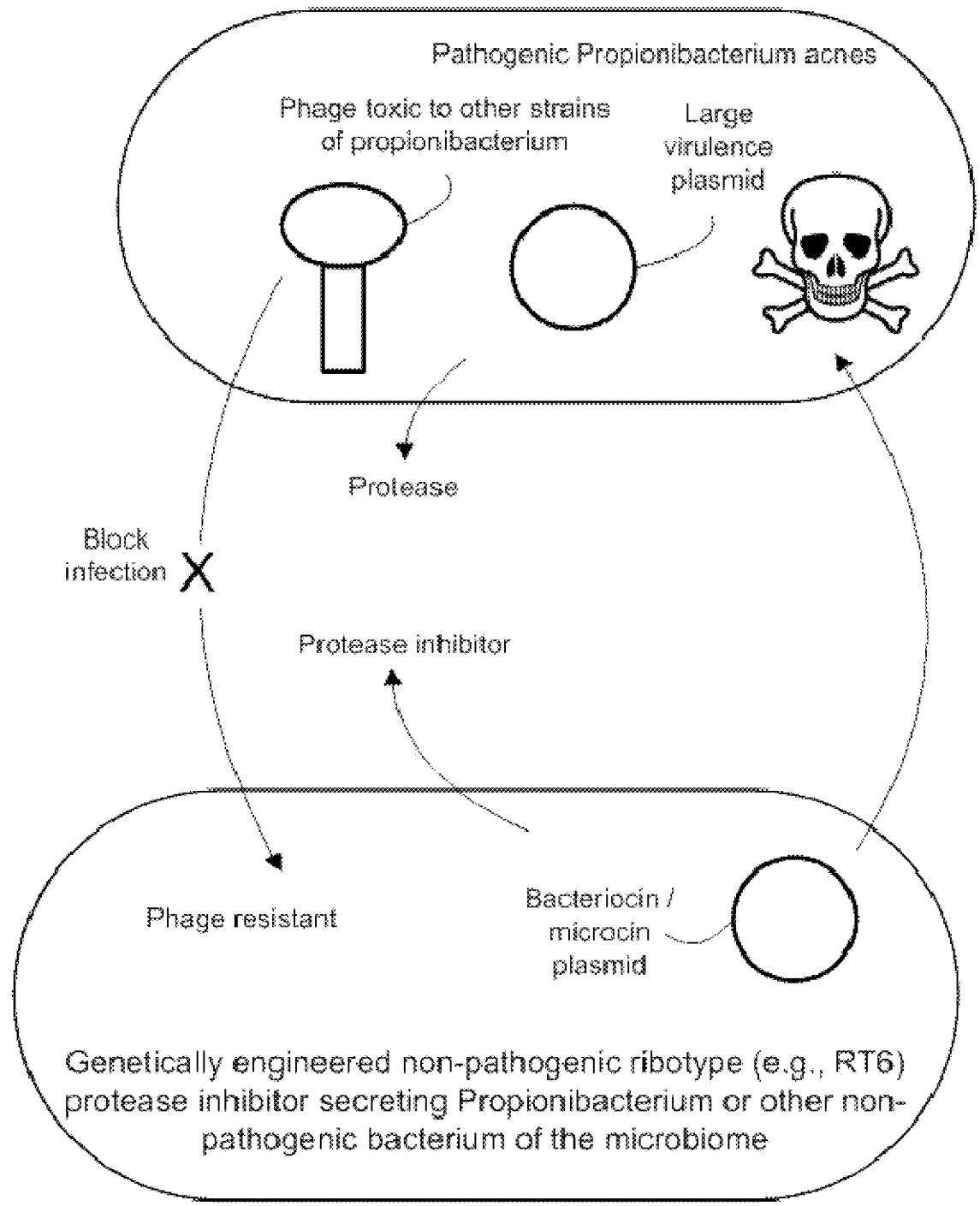
FIG. 6 shows a pathogenic *Propionibacterium acnes* and a non-pathogenic bacterium resistant to phage that produces a microcin that kills *Propionibacterium acnes*, respectively.

Optionally, the protease inhibitors may be known polypeptide inhibitors engineered to be expressed by the bacteria. The inhibitors include both synthetic peptides and naturally occurring, endogenous peptides and metabolites. To result in the desired activity, the peptides or metabolites should be surface displayed, released or secreted outside of the microorganism. Accordingly, the peptides are modified by fusing them to secretion signals. The secretion signals may be: N-terminal (LPP:OmpA, M13pIII, M13pIII with a signal recognition particle site, M13pVIII, zirS (Finlay et al., 2008, PLoS Pathogens 4 (4), e100003); heat-stable (ST; thermostable) toxins from Escherichia and Vibrio (U.S. Pat. No. 5,399,490, expressly incorporated herein by reference); E. coli enterotoxin II (Kwon et al., U.S. Pat. No. 6,605,697, expressly incorporated herein by reference); by colicin fusions together with colicin lysis proteins, or using autotransporter fusions; fusion to the M13 pIX may also be used (WO 2009/086116, expressly incorporated herein by reference); hlyA C-terminal signal sequence last 60 amino acids of the E. coli HlyA hemolysin, together with the required HlyBD supplied in trans and endogenous tolC as shown in FIG. 6.

The N-terminal signal sequences are well known and characterized by the presence of a protease cleavage site for an endogenous bacterial protease. Thus, N-terminal signal sequences provide free protease inhibitors, free from the signal sequence. The C-terminal signal sequence may be further engineered to have a protease cleavage site in between the protease inhibitory peptide and the signal sequence. The cleavage site may be for the same protease that the peptide inactivates. Thus, the protease activates its own inhibitor. The protease cleavage site may also be for a protease other than for the protease inhibitor, thus deactivating another protease. Multiple protease inhibitor peptides may be used in-frame with multiple protease cleavage signals (polymeric protease activated protease inhibitors), where the inhibitors alternate with cleavage sites.

The polymeric protease activated protease inhibitors can be homo- or hetero-inhibitor polymers (i.e., have inhibitors for the same or different proteases, respectively), and/or homo- or hetero-protease cleavage polymers (i.e., have the same or different protease cleavage sites). Proteases upregulated within tumors for which protease cleavage sites may be engineered include: tissue plasminogen activator, activated protein C, factor Xa, granzyme (A, B, M), cathepsin, thrombin, plasmin, urokinase, matrix metalloproteases, prostate specific antigen (PSA) and kallikrein 2 (e.g., Edwards et al. (eds) 2008, The Cancer Degradome: Proteases and Cancer Biology, Springer, 926 pp), as well as proteases of lysosomes and the gut.

Protease inhibitors have been reviewed by Laskowski and Kato, 1980, (Annual Review of Biochemistry 49: 593-626), expressly incorporated by reference herein. Serine proteases inhibitors, the largest group, include 1) bovine pancreatic trypsin inhibitor (Kunitz) family, 2) pancreatic secretory trypsin inhibitor (Kazal) family, 3) Streptomyces subtilisin inhibitor family, 4) soybean trypsin inhibitor (Kunitz) family, 5) soybean proteinase inhibitor (Bowman-Birk) family 6) potato I inhibitor family, 7) potato II inhibitor family, 8) Ascaris trypsin inhibitor family, and 9) others. Protease inhibitors have also been grouped within the MEROPS peptidase database (Rawlings et al., 2008 Nucleic Acids Res. 36 Database issue, D320-325). Specific examples of protease inhibitors that may be expressed as complete proteins or peptide fragments corresponding to the active inhibitory site include but are not limited to aprotinin, autodisplay aprotinin (Jose J, Zangen D (2005) Autodisplay of the protease inhibitor aprotinin in *Escherichia coli*. Biochem Biophys Res Commun 333:1218-1226; Jose, 2006, Autodisplay: efficient bacterial surface display of recombinant proteins, Appl Microbiol Biotechnol 69: 607-614), cathepsin inhibitor peptide sc-3130, lymphocyte protease inhibitor, maspin, matrix metalloprotease inhibitors, macroglobulins, antithrombin, equistatin, Bowman-Birk inhibitor family, ovomucoid, ovoinhibitor-proteinase inhibitors from avian serum, dog submandibular inhibitors, inter-a-trypsin inhibitors from mammalian serum, chelonianin from turtle egg white, soybean trypsin inhibitor (Kunitz), secretory trypsin inhibitors (Kazal) ai-proteinase inhibitor, *Streptomyces* subtilisin inhibitor, plasminostreptin, plasmin inhibitor, factor Xa inhibitor, coelenterate protease inhibitors, protease inhibitor anticoagulants, ixolaris, human Serpins (SerpinA1 (alpha 1-antitrypsin), SerpinA2, SerpinA3, SerpinA4, SerpinA5, SerpinA6, SerpinA7, SerpinA8, SerpinA9, SerpinA10, SerpinA11, SerpinA12, SerpinA13, SerpinB1, SerpinB2, SerpinB3, SerpinB4, SerpinB5, SerpinB6, SerpinB7, SerpinB8, SerpinC1 (antithrombin), SerpinD1, SerpinE1, SerpinE2, SerpinF1, SerpinF2, SerpinG1, SerpinNI1, SerpinNI2), cowpea trypsin inhibitor, onion trypsin inhibitor, alpha 1-antitrypsin, *Ascaris trypsin* and pepsin inhibitors, lipocalins, CI inhibitor, plasminogen-activator inhibitor, collagenase inhibitor, Acp62F from *Drosophila*, bombina trypsin inhibitor, *bombyx* subtilisin inhibitor, von Willebrand factor, leukocyte secretory protease inhibitor. Short peptide inhibitors of protease are preferred. Many protease inhibitors have one or more disulfide bonds. Fusion to thioredoxin (trxA) is known to improve protease inhibitor activity (e.g., Furuki et al., 2007, Fukuoka University Science Reports 37: 37-44). Fusion to glutathione-S transferase (GST) and co-expression with disulfide bond isomerase (DsbA) or NusA (Harrison 2000, Expression of soluble heterologous proteins via fusion with NusA protein. *inNovations* 11: 4-7) are also known to improve solubility. Methods to isolate novel protease inhibitors using M13 phage display have been described by Roberts et al., 1992 (Gene 121: 9-15). Neutrophil serine protease inhibitors derived from elafin (also known as trappin-2 or SKALP (skin-derived anti-leukoproteinase) which targets elastase and proteinase 3) and SLPI (which targets elastase and cathepsin G) have been described as polyvalent inhibitors of neutrophil serine proteases (Zani et al., 2009 Protease inhibitors derived from elafin and SLPI and engineered to have enhanced specificity towards neutrophil serine proteases, Protein Science 2009 18: 579-594). Koivunen et al., (1999 Tumor targeting with a selective gelatinase inhibitor, Nature Biotechnology 17: 768-774) have described a short peptide (CTTHWGFTLC SEQ ID: 003) inhibitory to MMP2 and MMP9 and Bjorklund et al. have described the leukocyte specific 3-2 integrin binding partner for pro-MMP-9 "DDGW" SEQ ID: 004 (Bjorklund et al., 2004 Peptide Inhibition of catalytic and noncatalytic activities of matrix metalloproteinase-9 blocks tumor cell migration and invasion, J. Biol. Chem. 279: 29589-29597). Other peptides include DX-88 which contains the Kunitz domain from human lipoprotein-associated coagulation inhibitor domain 1 (LACI-D1) or the variant DX-1000. Calpastatin and novel secreted derivatives including transmembrane transport (i.e., cell penetrating peptides or ferry peptides such as TAT (Heitz et al., 2009, Twenty years of cell-penetrating peptides: from molecular mechanisms to therapeutics Br J Pharmacol. 2009 May; 157(2): 195-206) described herein are also encompassed.

The peptide inhibitors are engineered to be secreted from the gram negative bacteria secretion signals known to those skilled in the arts and may optionally be engineered to contain a signal recognition particle translocation sequence Steiner et al., 2006, signal sequences directing cotranslational translocation expand the range of proteins amenable to phage display, Nature Biotechnol 24: 823-831), including *E. coli* cytolethal distending toxin, Shiga toxin, LPP:OmpA, M13pIII, M13pVIII, zirS (Finlay et al., 2008, PLoS Pathogens 4 (4), e100003), heat-stable (ST; thermostable) toxins from *Escherichia* and *Vibrio* (U.S. Pat. No. 5,399,490), *E. coli* enterotoxin II (Kwon et al., U.S. Pat. No. 6,605,697) N-terminal signal sequences, or hlyA C-terminal signal sequence (requires addition of hlyBD and TolC), or by colicin fusions together with colicin lysis proteins, or using autotransporter (autodisplay) fusions. The autotransporter surface display has been described by Berthet et al., WO/2002/070645, expressly incorporated by reference herein. Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999) demonstrated hybrid proteins containing the β-autotransporter domain of the immunoglobulin A (IgA) protease of Nisseria gonorrhea. Fusion to the M13 pIX may also be used (WO 2009/086116) or fusions to type III secretion system of *Salmonella* or other bacteria (Wilmaier et al., 2009 Mol Sys Biol 5: 309. The inhibitors can be further modified to have the protease cleavage signal of the protease that they inhibit or for a different protease. Secretion signal from gram positive bacteria include that from listerialysin O (LLO), alkaline phosphatase (phoZ) (Lee et al., 1999, J Bacteriol. 181: 5790-5799), CITase gene (Shiroza and Kuramitsu 1998, Methods in Cell Science, 20: 127-136) or the twin arginine translocation system (Berks et al., 2005, Protein targeting by the bacterial twin-arginine translocation (Tat) pathway, Current Opinion in Microbiology 8: 174-181). Enhanced secretion may be achieved as described in U.S. Pat. No. 7,358,084, WO/2009/139985 Methods and materials for gastrointestinal delivery of a pathogen toxin binding agent; van Asseldonk, M et al. 1990, Cloning of usp45, a gene encoding a secreted protein from *Lacotococcs lactis* subsp. *lactis* MG1363 Gene 95, 15-160; Kim et al., Display of heterologous proteins on the surface of *Lactococcus lactis* using the H and W domain of PrtB from *Lactobacillus delburueckii* subsp. *bulgaricus* as an anchoring matrix J Appl Microbiol. 2008 June; 104(6):1636-43. Epub 2008 Feb. 19).

The proteins may have one or more additional features or protein domains known to those skilled in the art which are designed to be active or catalytic domains that facilitate them being secreted or released by autolytic peptides such as those associated with colicins or bacteriophage release peptides or thioredoxin or glutathione S-transferase (GST) fusions that improve solubility.

5.3 Bacteriocins, Production and Resistance, and Resistance to Phage

In one embodiment, the probiotic bacteria express one or more bacteriocins and one or more bacteriocin immunity proteins. In another embodiment, the bacteria co-expresses a protease inhibitor and bacteriocin/bacteriocin immunity proteins. Bacteriocins (bacterially produced antibacterial agents that inhibit other strains of bacteria but not the host strain that produces them), such as lactococcins, microcins or colicins (Riley and Chavan 2006, Bacteriocins: Ecology and Evolution, Springer; de Vuyst and Vandamme 2012, Bacteriocins of lactic acid bacteria; Microbiology, genetics and applications, Blackie Academic & Professional Press). In a more preferred embodiment, the bacteriocin is the acnecin from *Propionibacterium acnes* (Fujimura and Nakamura 1978) or the bacteriocin from *Propionibacterium shermanii* (Ayers et al., *Propionibacteria* peptide microcin U.S. Pat. No. 5,635,484 A), the bacteriocin from *Streptococcus salivarius* (Bowe et al., 2006, J. Drugs Dermatol 5: 868-870), the bacteriocin from *Lactococcus* sp. HY 449 (Oh et al., 2006. Effect of bacteriocin produced by *Lactococcus* sp HY 449 on skin inflammatory bacteria, Food Chem Toxicol 44: 1184-1190) or the bacteriocin from *Lactococcus* sp. HY 49 or *Lactobacillus casei* HY 2782 described by Kim et al., (U.S. Pat. No. 6,329,002 Food for inhibiting infection and treating gastritis, gastric and duodenal ulcers). In most preferred embodiment, the probiotic bacterium is a *Propionibacteria acnes* of ribotype 6 (RT6) associated with normal skin (Fitz-Gibbon, S. et al., 2013 *Propionibacterium acnes* Strain Populations in the Human Skin Microbiome Associated with Acne, Journal of Investigative Dermatology 133:2152-60) that expresses an anti-*Propionibacterium acnes* bacteriocin effective against ribotypes associated with acne such as RT4, 5, 7, 8, 9 & 10 (Fitz-Gibbon et al., 2013), such that the bacteriocin allows the normal skin *P. acnes* to penetrate into the skin and overtake the population of *P. acnes* associated with acne due to the ability of the bacteria of the invention to be immune to acne-associated strain's bacteriocin, and thus can kill and occupy the acne-producing strains location, thereby reducing or eliminating the symptoms of acne.

The bacteria may be further selected for enhanced bacteriocin production using standard methods for visualizing production of bacteriocins which uses an indicator strain usually embedded in a soft agar overlay, and a test strain, or library or mixed population of strains, applied to the surface. The production of the bacteriocin is then visualized as an increased zone of inhibition of the indicator strain. Using methods known to those skilled in the arts which include various mutagenesis methods such as exposure to ultraviolet light, chemical mutagens such as nitrosoguanidine, or genetic methods such as over expression on plasmids, insertion of strong promoters, transposon mutagenesis, organisms with improved production of bacteriocins are visualized as producing wider zones of bacterial inhibition.

Resistance to phage by the *Propionibacteria acnes* RT6, and many other bacteria species, is already understood to occur, at least in part, by the CRISPER (Clustered Regularly Interspaced Short Palindromic Repeats) systems, but the "immunity" may be incomplete, and could allow phage from resident pathogenic bacteria to kill the probiotic bacterium, preventing it from having as fully effective therapeutic action. The bacteria of the invention may be further engineered to have phage resistance proteins, such as phage repressor proteins related to lambda phage c repressor, including those identified by Marinelli, et al., 2012 (*Propionibacterium acnes* Bacteriophages Display Limited Genetic Diversity and Broad Killing Activity against Bacterial Skin Isolates, mBio 3(5) doi:10.1128/mBio.00279-1). These authors suggest the possible use of the phage as a form of "phage therapy", i.e., to kill *Propionibacterium acnes*, but do not propose or suggest the use of the *Propionibacterium acnes*, or phage-resistant bacteria, or bacteria with bacteriocins, or bacteria with bacteriocins and protease inhibitors as an effective form of therapy for acne. Use of standard methods of isolating and/or identifying phage resistant strains is also encompassed. It is of importance that the therapeutic bacterial strain, such as the RT6 strain of *Propionibacterium acnes*, be resistant to the resident, disease-associated organisms such as pathogenic ribotypes RT4, 5, 7, 8, 9 & 10 of *Propionibacterium acnes* (Fitz-Gibbon et al., 2013) or bacteria such as *Staphylococcus aureus* or *Streptomyces pyogenes*. Methods for selecting resistant strains selection for spontaneous resistance by exposure of the strain such as RT6 to the phage such as those described by Marinelli, et al., 2012 (*Propionibacterium acnes* Bacteriophages Display Limited Genetic Diversity and Broad Killing Activity against Bacterial Skin Isolates, mBio 3(5) doi: 10.1128/mBio.00279-1), and recovery of the survivors, or the strain can be initially modified by chemical, ultraviolet or transposon mutagenesis, to create a mixed genetic population followed by exposure to the phage, and selection of survivors (Levin, 1994, Isolating multiple strains of *Escherichia coli* for coliphage isolation, phage typing, and mutant recovery, Chapter 4 pages 63-72, in Tested studies for laboratory teaching, Volume 15 (C. A. Goldman, Editor). Proceedings of the 15th Workshop/Conference of the Association for Biology Laboratory Education (ABLE), 390 pages; Exploitation of a new flagellatropic phage of *Erwinia* For positive selection of bacterial mutants attenuated in plant virulence: towards phage therapy T. J. Evans, J Appl Microbiol 108 (2010) 676-685). The surviving strains may contain genetically integrated phage, i.e., lysogens. Preferred strains are those that do not contain the phage, which is readily determinable by genetic techniques such as PCR. Similar techniques are used to select therapeutic strains that are resistant to the bacteriocins of pathogenic strains.

The resulting bacteria are both capable of resisting attack by the virulent bacterial bacteriocins and/or their phage, are able to persist, colonize and kill pathogenic ribotypes by expressing bacteriocins the pathogens are sensitive to, and secrete protease inhibitors that suppress inflammation.

5.4 Antibody Expressing Bacteria

In another embodiment, the probiotic bacteria displays an anti-inflammatory antibody, such as anti-TNF-alpha antibody, TNF-beta antibody, anti-IL-12, IL-17 or IL-23 antibody, either by surface display (Nhan et al., 2011 Surface display of *Salmonella* epitopes in *Escherichia coli* and *Staphylococcus carnosis*, Microbial Cell Factories 2011, 10:22; Lee et al., 2003, Microbial Surface Display, Trends in Biotechnology 21: 45-52; Kramer et al., 2003, Autodisplay: Development of an efficacious system for surface display of antigenic determinants in *Salmonella* vaccine strains, Infec. Immun. 71: 1944-1952) or by carrying a phage that displays the antibody when secreted. The microbiome, probiotic, commensal or attenuated pathogenic bacterium may be either gram negative, such as *E. coli*, or gram positive, such as *Lactococcus* sp. or *Lactobacillus* sp. isolated from the human microbiome. The gram negative bacteria may express and secrete an anti-TNF antibody as an autotransporter display protein or a pIII fusion on a phage such as those derived from M13, fd and other filamentous phage. The Gram positive bacteria will express and secrete an anti-TNF antibody such as an M13 pIII homolog fusion (p6 on a phage such as that derived from B5; Chopin et al. 2005). The antiTNF single chain antibody can be one such as described by Mukai et al., 2006; Yang et al., 2010) and may be fully humanized (United States Patent Application 2012/0308575, expressly incorporated herein by reference).

5.5 Determination of Synergy

Overall improvement is defined as an increase in effect, such as the ability to inhibit inflammatory disease symptoms. The contribution of the enhanced protease inhibitor production with bacteriocin production is determined individually and in combination. Additivity, synergy or antagonism may determined using the median effect analysis (Chou and Talaly 1981 Eur. J. Biochem. 115: 207-216) or other standard methods and used to select improved bacteria with optimal combinations in their ability to suppress inflammation.

6. FIGURE LEGEND

FIG. 1 shows a stepwise procedure for detecting protease inhibitors.

Figure 2A:
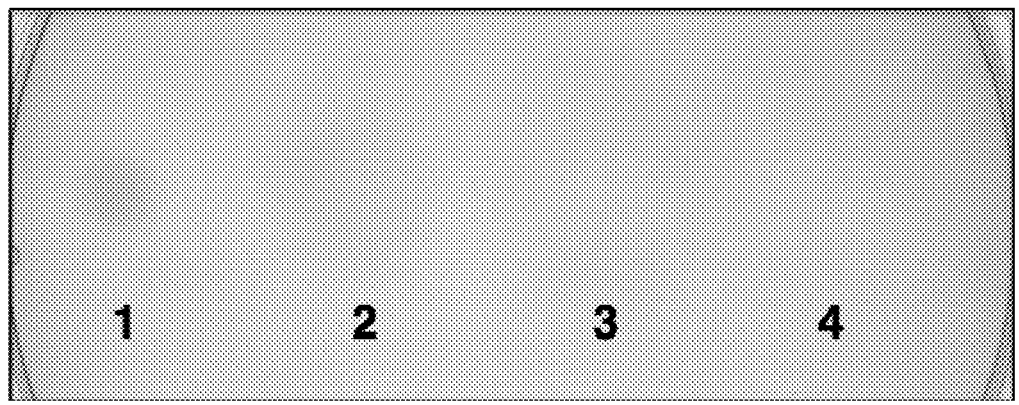
FIGS. 2A and 2B show protease inhibitor zones of protease protection.
Figure 2B:
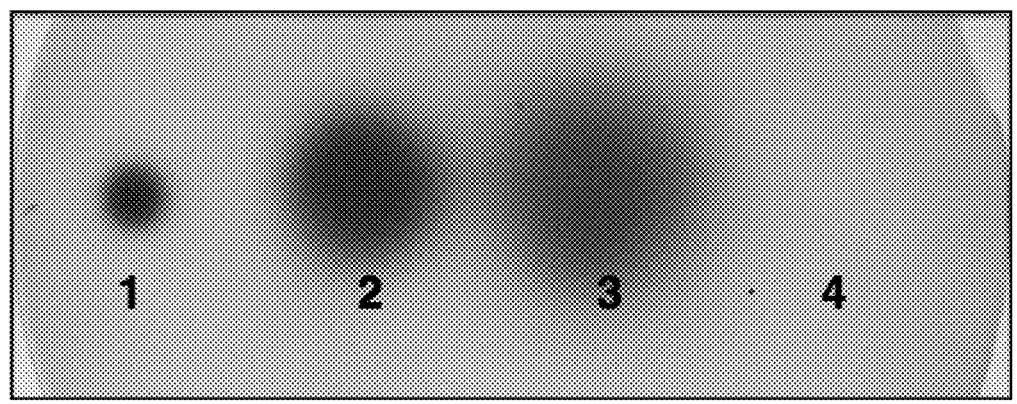

FIGS. 2A and 2B show protease inhibitor zones of protease protection. Protease inhibitors were pipetted onto the surface of a casein plate containing BCG. After 1 hour the plate was flooded with 1.0 ml of sterile-filtered 0.625 mg/ml trypsin and allowed to absorb, followed by addition of 1 ml carbenicillin/streptomycin and incubation at 37° C. overnight. FIG. 2A shows the BCG containing plate prior to PS staining and FIG. 2B shows the same plate following PS staining and destaining. 1) α-2-macroglubulin (2 ml of 7.8 mg/ml in $dH_2O$), 2) aprotinin (2 ml of 0.3 mM in sterile $dH_2O$), 3) leupeptin (2 ml of 10 mM in sterile $dH_2O$), and 4) bestatin (2 ml of 1 mM in methanol).

Figures 3A, 3B:
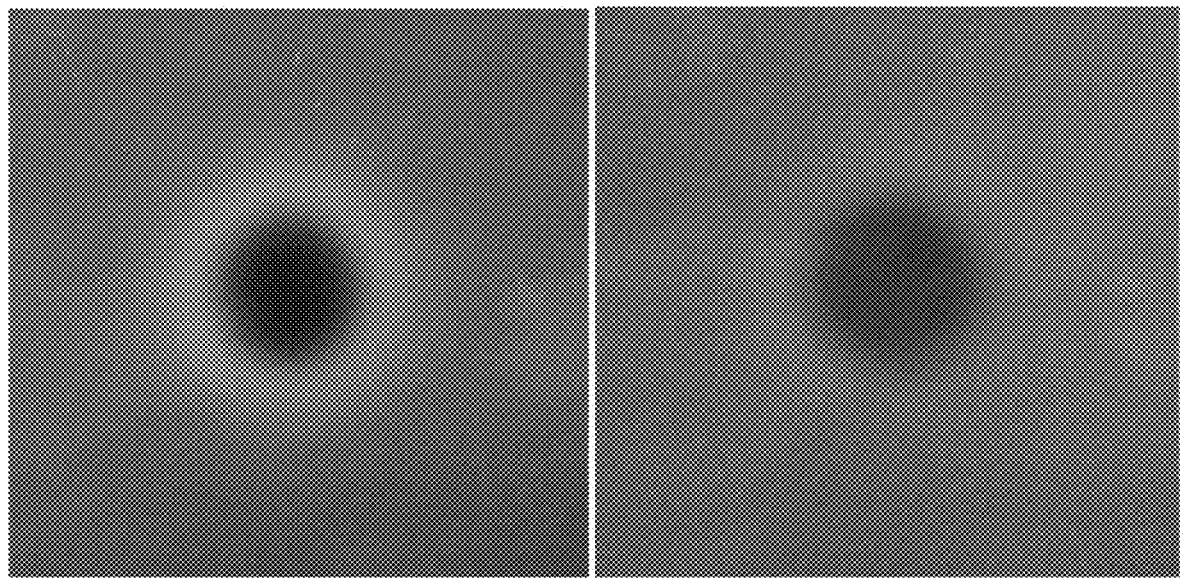
FIGS. 3A and 3B show protease inhibitor precipitation zone.

FIGS. 3A and 3B show protease inhibitor precipitation zones. The aprotinin protease protection zones were visibly distinct under conditions of increased amounts of trypsin on the different protein containing plates. FIG. 3A) Aprotinin (2 ml of 0.3 mM in sterile $dH_2O$) with 2.5 mg/ml trypsin on a BCG gelatin plate and FIG. 3B) aprotinin (2 ml of 0.3 mM in sterile $dH_2O$) with 2.5 mg/ml trypsin on a BCG casein plate.

Figure 4:
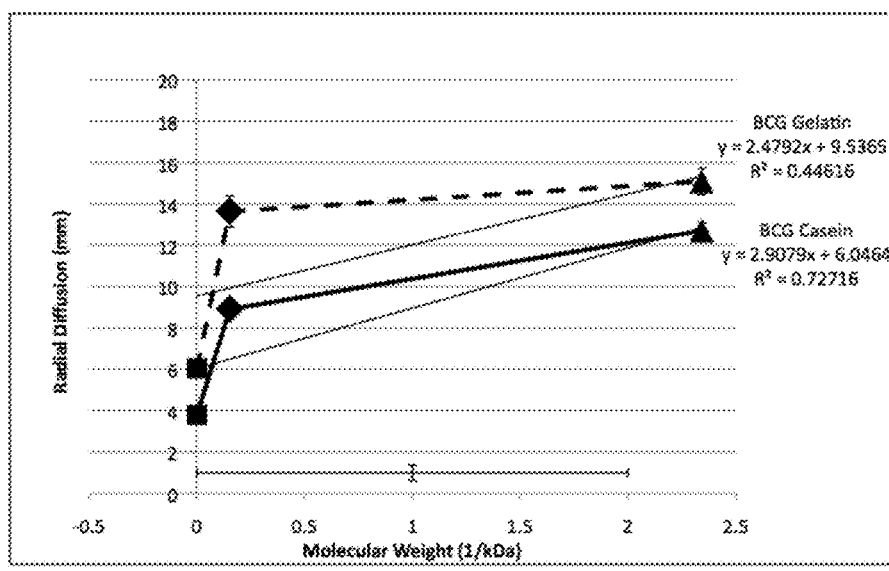
FIG. 4 shows correlation of the protease inhibitor molecular mass with the diffusion zone that creates the zone of protease protection.

FIG. 4 shows correlation of the protease inhibitor molecular mass with the diffusion zone that creates the zone of protease protection. The inhibition zones created by the three trypsin inhibitors were plotted as the radius against the inverse molecular mass of the inhibitors (α-2-macroglobulin, ~720 kDa; aprotinin, 6511 Da; and leupeptin 427 Da). $R^2$ linear regression was inserted using Microsoft Excel. Dotted line, BCG gelatin; solid line, GCG casein.

FIGS. 5A and 5B show bacterial protease inhibitor zones of protease protection. The bacteria were grown for 2 days at 30° C. on casein plates with BCG. The bacteria were gently washed off and the plate flooded with 1.0 ml of sterile-filtered 0.625 mg/ml trypsin and allowed to absorb, followed by addition of 1 ml carbenicillin/streptomycin and incubation at 37° C. overnight. The plate was further stained with Ponseau S and then destained in water overnight. FIG. 5A shows the Growth pattern of the colonies on the BCG plate containing casein following incubation at 30° C. FIG. 5B shows PS staining pattern of the same plate. 1) *Photorhabdus luminescens* 1° form, 2) *Photorhabdus luminescens* 2° form, 3) *Citrobacter freundii* B, 4) *S. epidermidis*, 5) *S. aureus*, 6) *Enterococcus fecalis*, α2m) α-2-macroglubulin.

FIG. 6, upper portion, shows a pathogenic *Propionibacterium acnes* carrying phage and a virulence associated plasmid that secretes one or more proteases.

FIG. 6, lower portion, shows a non-pathogenic genetically engineered probiotic *Propionibacterium*, or any other non-pathogenic bacterium of the microbiome engineered to have the properties that it is resistant to the phage from the pathogenic form, can kill the pathogenic form with a bacteriocin/microcin and optionally, secretes a protease inhibitor to reduce inflammation.

7. EXAMPLES

In order to more fully illustrate the invention, the following examples are provided.

Example 1: A Novel Technique for Detection of Secreted Microbial Protease Inhibitors The overall procedure is shown in FIG. 1. Because the protocol is destructive to the plate assayed, a duplicate or replica plate is generated and retained for identification and further analysis of the strains using methods known to those skilled in the arts. The initial step is the exposure of the protease detection plate to a protease inhibitor or bacterial growth. Either commercially available protease inhibitor peptides or growth of bacterial strains on the protease detection plates can be detected. Protease inhibitors include α-2-macroglobulin (7.8 mg/ml in sterile water; Thermo Fisher), aprotinin (0.3 mM in sterile $dH_2O$; Thermo Fisher), leupeptin (10 mM in sterile $dH_2O$; Thermo Fisher), and bestatin (1 mM in methanol; Thermo Fisher) that are pipetted as 2.0 ml drops onto the surface of the protein containing plates and allowed to be absorbed into the plate and diffuse for 1 hour. The bacterial strains *Photorabdus* (*Xenorhabdus*) *luminescens* strain Hm primary and secondary forms where the secondary and not the primary form is known to secrete a protease inhibitor and the other strains are negative controls (Wee et al. 2000, A new broad-spectrum protease inhibitor from the entomopathogenic bacterium *Photorhabdus luminescens*. Microbiology 146: 3141-3147), *Citrobacter freundii* (ATCC #33128), *Staphylococcus aureus*, *S. epidermidis* and Enterococcusfaecalis are allowed to grow two days at 30° C. in air.

The base media can be any microbiological media designed to facilitate the growth of cultivable microorganism; different media can be used to favor different strains as appropriate (Kreig, 1981, Chapter 8, Enrichment and Isolation, p. 112-142 in Manual of Methods for General Bacteriology, Gerhardt et al., eds, American Society for Microbiology, Washington, D.C.). Variations on the type of protease being targeted, the protease substrate and cognate inhibitors are shown in Table 1 and used as a guide in the modification of media. A casein base media based on that of Vijayaraghavan and Vincent (2013, A simple method for the detection of protease activity on agar plates using bromochresol green dye, J. Biochem. Tech. 4: 628-630), which contained 5 grams of peptone, 1.5 grams of yeast extract, 1.5 grams of sodium chloride per liter with, except that the casein 0.5% is used (instead of 1.0%) and dissolved as described by Montville (1983, Dual-substrate plate diffusion assay for proteases, Appl Environ Microbiol 45: 200-204) using 0.02 N NaOH. When bromochresol green (BCG) is added directly to the media, 0.0015% is used. BCG preincorporated into the media as well as post incubation addition of a BCG dye reagent containing 0.028% BCG dissolved in 0.56% (w/v) succinic acid, 0.1% (w/v) NaOH (Vijayaraghavan and Vincent; 2013) with 0.6% Brij-35 and then acidified to pH 4.2 can also be used following exposure to a protease inhibitor or bacterial growth and subsequent exposure to a protease. After staining and then destaining in water the by completely removing the agar from the lower plastic, the plates are observed for the presence and absence of protein. Ponseau S staining by flooding the plate with 5 ml of the stain containing 0.1% Ponseau S (PS; Sigma, St. Louis, Mo.) and 5% acetic acid in water for 1-2 hrs and then marking the agar with a 23 ga syringe needle dipped in India ink at a corresponding register marked on the plastic petri plate, removing the agar from the plate and destaining overnight in water before observing them and is highly sensitive.

A gelatin based media (Medina and Baresi 2007, Rapid identification of gelatin and casein hydrolysis using TCA, J Microbiol Meth 69: 391-393) which uses 40 grams per liter of tryptic soy agar powder without glucose (Becton Dickinson, Sparks, Md.) modified to contain 8 g of gelatin (instead of 16 g) per liter may be preferable for certain organisms depending upon their growth requirements and is used as is appropriate. Approximately 5 ml of 20% trichloroacetic acid (TCA; Thermo Fisher, Waltham, Mass.) was used for protein precipitation per petri plate. This media can also be combined with preincorporated BCG, or post-incubation BCG dye reagent or Ponseau S, each as described above for the casein plates.

Following incubation, the bacterial strains are washed off the plate using a gentle stream of water in order to remove the colonies and eliminate their potential for surface inhibition effects on diffusion of the protease and/or dyes. The next step is to expose the plate to a protease-containing solution to cause clearing of the substrate (Table 1; FIG. 1). Casein-containing plates required a higher concentration of trypsin to achieve clearing, using trypsin concentrations as high as 2.5 mg/ml. The plates are flooded with either 1.0 ml of sterile-filtered 0.625 mg/ml trypsin or 0.0625 mg/ml trypsin in 10 mM Tris 1 mM EDTA pH 8.0 for casein and gelatin respectively, and allowed to incubate at 37° C. overnight. After the trypsin is absorbed into the plate (20-60 min.), 1 ml of sterile filtered water containing 2.5 mg carbenicillin and 750 mg streptomycin is also allowed to absorb into the plate in order to stop any further bacterial growth.

In order to detect the zones of protease inhibition, the plates are observed for the presence of opaque zones surrounded by clearing that are detected with TCA precipitation as per Medina and Baresi 2007 (Rapid identification of gelatin and casein hydrolysis using TCA. J. Microbiol. Meth. 69: 391-393) or by bromochrosol green (BCG) previously incorporated into the media (Vijayaraghavan and Vincent. 2013, A simple method for the detection of protease activity on agar plates using bomochresolgreen dye, J. Biochem. Tech. 4: 628-630), or by the addition Ponseau S dye. Radial diffusion is measured in triplicate, entered into Microsoft Excel, plotted, and analyzed using linear regression.

A comparison of the different variations on protein substrates, dyes and destains is shown in Table 1. Following the addition of a protease inhibitor and its diffusion into the plate, the majority of the protein contained within the plates is subsequently hydrolyzed by the addition of the protease trypsin. However, in the presence of the protease inhibitors, a zone of protection against proteolysis is created. When the plates are observed for the presence of protein either by TCA precipitation or the localized concentration of a dye such as BCG or PS, a zone of unhydrolyzed protein is observed in the location of the protease inhibitor. Using α-2-macroglobulin, aprotinin, leupeptin and bestatin we found that we were only able to faintly visualize the α-2-macroglobulin and aprotinin on the casein plates with preincorporated BCG (FIG. 2A). However, the combination of BCG-containing plates further stained with PS is the most sensitive when 0.625 mg/ml trypsin was used for casein and 0.0625 mg/ml trypsin was used for gelatin (Table 5; FIG. 2B). Using those plates and staining procedure we are able to visualize all three of the trypsin inhibitors α-2-macroglobulin, aprotinin, and leupeptin, with no staining for bestatin. Differences in a white ring of protein precipitation were observed that occurred strongly on the gelatin plates when higher concentrations of trypsin (2.5 mg/ml) were used, but only slightly on the casein plates when they were treated with the same trypsin concentration (FIGS. 3A and 3B). It was also observed on the casein plates, but to a lesser degree the gelatin plates, that the zone of inhibition for leupeptin (427 Da) was notably larger than the zone of inhibition for aprotinin (6511 Da), or that of the α-2-macroglobulin (~720 kDa) which had the smallest diffusion zone (FIGS. 2A and 2B). When the radius was measured and plotted against the inverse of the molecular mass, a general relationship of size and diameter was also apparent for the casein plates and to a lesser degree for the gelatin plates (FIG. 4). An $R^2$ regression analysis was performed using Microsoft Excel, but the results were not significant for either the casein plates (R2=0.73) or the gelatin plates (R2=0.47). The relative intensity of the zone of inhibition based on different amounts of protease inhibitor allows for observation and selection of strains producing the most inhibitor.

Analysis of the six bacterial strains, *Photorabdus luminescens* Hm primary and secondary forms, *Citrobacter freundii, Staphylococcus aureus, S. epidermidis* and *Enterococcus faecalis* showed that the *Photorabdus luminescens* Hm secondary form, and not the primary form, was protease inhibitor positive (FIGS. 5A and 5B). These results were therefore consistent with previous results (Schmidt et al., 1988; Woo et al, 2000). The *P. luminescens* secondary form colony grew fairly large (FIG. 5A), and it was apparent that the inhibitor only diffused a short distance from the edge of the colony. Likewise, the α-2-macroglobulin also diffused only a short distance. These data establish the capability of this novel assay to detect protease inhibitors from large numbers of bacteria growing in mixed populations on petri plates.

TABLE 5

Protease inhibitor detection efficiency, protein substrates, dyes and destaining.

| Variation | Protein Substrate | Dye incorporated in plate | Dye or Reagent added after growth | Destain | Relative Detection Efficiency | | |
|---|---|---|---|---|---|---|---|
| | | | | | α-2 Macroglobulin | Aprotonin | Leupeptin |
| 1 | 0.5% Casein | None | BCG | 1 hour Water | + | +/− | +/− |
| 2 | 0.5% Casein | None | Ponseau S | Overnight Water | +++ | +++ | +++ |

TABLE 5-continued

Protease inhibitor detection efficiency, protein substrates, dyes and destaining.

| Variation | Protein Substrate | Dye incorporated in plate | Dye or Reagent added after growth | Destain | Relative Detection Efficiency | | |
|---|---|---|---|---|---|---|---|
| | | | | | α-2 Macroglobulin | Aprotonin | Leupeptin |
| 3 | 0.5% Casein | None | TCA | 15 min development | + | +/− | +/− |
| 4 | 0.5% Casein | BCG | BCG | 1 hour Water | + | + | +/− |
| 5 | 0.5% Casein | BCG | Ponseau S | Overnight Water | +++ | +++ | +++ |
| 6 | 0.5% Casein | BCG | TCA | 15 min development | +/− | +/− | +/− |
| 7 | 0.8% Gelatin | None | BCG | 1 hour Water | − | − | − |
| 8 | 0.8% Gelatin | None | Ponseau S | Overnight Water | +++ | +++ | +++ |
| 9 | 0.8% Gelatin | None | TCA | 15 min development | +++ | +++ | +++ |
| 10 | 0.8% Gelatin | BCG | BCG | 1 hour Water | − | − | − |
| 11 | 0.8% Gelatin | BCG | Ponseau S | Overnight Water | +++ | +++ | +++ |
| 12 | 0.8% Gelatin | BCG | TCA | 15 min development | +++ | +++ | +++ |

Example 2: Isolation of Microorganisms with Inhibitors of Chymase

Mixed microbial organisms such as environmental samples, microbiome, mutant populations, or DNA libraries of microorganisms are plated to microbiological support media, with or without a membrane support which may be transferred from a media to an assay support at a microbial density that allows spatial distinction or localized enrichment of the bacteria on that support. Typically, an 85 mm Petri plate would display 300 to 3000 individual colonies; fewer or greater microbial colonies could be used.

The media may also be modified to be selective for various groups of microorganisms, such as salt tolerance (e.g., *Staphylococcus* growth on mannitol salt agar), or the addition of antibiotics such as cyclohexamide and nystatin at various concentrations (e.g., for selective growth of Actinomycetes and *Streptomyces* by addition of various antibiotics known to those skilled in the arts; Williams and Davies 1965, Use of antibiotics for selective isolation and enumeration of Actinomycetes in soil, J. Gen. Microbiol. 38: 251-261; Zhang, J. 2011, Improvement of an isolation medium for Actinomycetes. Modern Applied Science. 5 (2) 124-127; Seong et al., 2001, An improved selective isolation of rare Actinomycetes from forest soil, The Journal of Microbiology 39: 17-23), or the isolation of *Propionibacterium* on lactate and other isolation techniques (Kreig, 1981, Chapter 8, Enrichment and Isolation, p. 112-142 in Manual of Methods for General Bacteriology, Gerhardt et al., eds, American Society for Microbiology, Washington, D.C.).

Growth conditions may also be varied, including temperatures above the normal body temperature (e.g., 37 C for humans) such as 42 C, or below normal temperature such as 30 C. The atmospheric conditions of oxygen may be normal atmospheric, microaerophilic, hypoxic or anaerobic.

One or more media may be employed in one or more environmental conditions for the same biological sample, subdivided for each of the media and conditions, and modified as per Table 2. By way of example, a mixed bacterial population of the human skin microbiome is obtained by a skin swab plated at a density of approximately 1000 bacterial colonies per 85 mm Petri plate with tryptic soy agar media incubated in a 5% CO2/air chamber at 35 C for 16 hours. The tryptic soy agar (Difco Manual Difco & BBL Manual: Manual of Microbiological Culture Media, Second Edition, M. J. Zimbro et al., (Eds), Becton Dickinson and Co., 2009) and either N-Succinyl-Ala-Ala-Pro-Phe p-nitroanilide (3 μL/ml of Sigma Aldrich Cat. No. S0448) or 1 micromole of benzoyl-L-tyrosine ethyl ester (BTEE). The following day the bacteria are replica plated by methods known to those skilled in the arts (e.g., Lederberg, J and Lederberg, E M, 1952, Replica plating and indirect selection of bacterial mutants. J Bacteriol. 63: 399-406) to serve as a master plate from which the bacteria may be preserved as live and/or DNA samples such that those of interest can be individually identified and used for further study. The bacteria are then removed, either by removing their porous membrane support or by washing the bacteria off. The plate is then exposed to a chymase containing solution (0.5-1.0 U/ml) by addition to the surface of the plate, which is then allowed to adsorb into the petri plate and incubate.

N-Succinyl-Ala-Ala-Pro-Phe p-nitroanilide is a colorimetric substrate yielding a product with absorbance at 405 nm, a blue/violet color. After the purified chymase is added to the entire plate and allowed to cleave the the N-Succinyl-Ala-Ala-Pro-Phe p-nitroanilide, the plate is then observed for zones of decreased blue/violet absorption (lack of the N-Succinyl-Ala-Ala-Pro-Phe p-nitroanilide activation) compared to the surrounding areas where the chymase has activated the N-Succinyl-Ala-Ala-Pro-Phe p-nitroanilide and increased the absorbance. The lighter areas associated with particular bacterial colonies correspond to ones producing one or more chymase inhibitors.

The chymase enzyme also has the ability to degrade BTEE to N-Benzoyl-L-Tyrosine+Ethanol, which increases the absorption at 256. When BTEE is used, the plate is then observed at or near 256 nm ultraviolet light for zones of decreased absorption compared to the surrounding areas where the chymase has degraded the BTEE and increased the absorbance. The lighter areas associated with particular bacterial colonies correspond to ones producing one or more chymase inhibitors.

Example 3: Isolation of Microorganisms with Inhibitors of Calpain

Mixed microbial organisms such as environmental samples, microbiome, mutant populations, or DNA libraries of microoganisms are plated to microbiological support media, with or without a membrane support which may be transferred from a media to an assay support at a microbial density that allows spatial distinction or localized enrichment of the bacteria on that support. Typically, an 85 mm Petri plate would display 300 to 3000 individual colonies; fewer or greater microbial colonies could be used.

The media may also be modified to be selective for various groups of microorganisms, such as salt tolerance (e.g., *Staphylococcus* growth on mannitol salt agar), or the addition of antibiotics such as cyclohexamide and nystatin at various concentrations (e.g., for selective growth of Actinomycetes and *Streptomyces* by addition of various antibiotics known to those skilled in the arts; Williams and Davies 1965, Use of antibiotics for selective isolation and enumeration of Actinomycetes in soil, J. Gen. Microbiol. 38: 251-261; Zhang, J. 2011, Improvement of an isolation medium for Actinomycetes. Modern Applied Science. 5 (2) 124-127; Seong et al., 2001, An improved selective isolation of rare Actinomycetes from forest soil, The Journal of Microbiology 39: 17-23), or the isolation of *Propionibacterium* on lactate and other isolation techniques (Kreig, 1981, Chapter 8, Enrichment and Isolation, p. 112-142 in Manual of Methods for General Bacteriology, Gerhardt et al., eds, American Society for Microbiology, Washington, D.C.).

Growth conditions may also be varied, including temperatures above the normal body temperature (e.g., 37 C for humans) such as 42 C, or below normal temperature such as 30 C. The atmospheric conditions of oxygen may be normal atmospheric, microaerophilic, hypoxic or anaerobic.

One or more media may be employed in one or more environmental conditions for the same biological sample, subdivided for each of the media and conditions. By way of example, a mixed bacterial population of the human skin microbiome is obtained by a skin swab plated at a density of approximately 1000 bacterial colonies per 85 mm Petri plate with tryptic soy agar media incubated in a 5% C02/air chamber at 35 C for 16 hours. The tryptic soy agar (Difco Manual Difco& BBL Manual: Manual of Microbiological Culture Media, Second Edition, M. J. Zimbro et al., (Eds), Becton Dickinson and Co., 2009).

The procedure of Example 2 is modified for calpain as indicated in Table 1.

Example 4: Isolation of Microorganisms with Inhibitors of Caspase-1

Mixed microbial organisms such as environmental samples, microbiome, mutant populations, or DNA libraries of microoganisms are plated to microbiological support media, with or without a membrane support which may be transferred from a media to an assay support at a microbial density that allows spatial distinction or localized enrichment of the bacteria on that support. Typically, an 85 mm Petri plate would display 300 to 3000 individual colonies; fewer or greater microbial colonies could be used.

The media may also be modified to be selective for various groups of microorganisms, such as salt tolerance (e.g., *Staphylococcus* growth on mannitol salt agar), or the addition of antibiotics such as cyclohexamide and nystatin at various concentrations (e.g., for selective growth of Actinomycetes and *Streptomyces* by addition of various antibiotics known to those skilled in the arts; Williams and Davies 1965, Use of antibiotics for selective isolation and enumeration of Actinomycetes in soil, J. Gen. Microbiol. 38: 251-261; Zhang, J. 2011, Improvement of an isolation medium for Actinomycetes. Modern Applied Science. 5 (2) 124-127; Seong et al., 2001, An improved selective isolation of rare Actinomycetes from forest soil, The Journal of Microbiology 39: 17-23), or the isolation of *Propionibacterium* on lactate and other isolation techniques (Kreig, 1981, Chapter 8, Enrichment and Isolation, p. 112-142 in Manual of Methods for General Bacteriology, Gerhardt et al., eds, American Society for Microbiology, Washington, D.C.)

Growth conditions may also be varied, including temperatures above the normal body temperature (e.g., 37 C for humans) such as 42 C, or below normal temperature such as 30 C. The atmospheric conditions of oxygen may be normal atmospheric, microaerophilic, hypoxic or anaerobic.

One or more media may be employed in one or more environmental conditions for the same biological sample, subdivided for each of the media and conditions. By way of example, a mixed bacterial population of the human skin microbiome is obtained by a skin swab plated at a density of approximately 1000 bacterial colonies per 85 mm Petri plate with tryptic soy agar media incubated in a 5% C02/air chamber at 35 C for 16 hours. The tryptic soy agar (Difco Manual Difco& BBL Manual: Manual of Microbiological Culture Media, Second Edition, M. J. Zimbro et al., (Eds), Becton Dickinson and Co., 2009).

The procedure of Example 1 is modified for Caspase-1 as indicated in Table 2. The YVAD-AFC emits blue light (400 nm) upon cleavage of the substrate by caspase-1; thus the petri plates are observed for areas that lack blue light emission.

Example 5: Isolation of Microorganisms with Inhibitors Neutrophil Serine Protease Elastase Inhibitors Mixed microbial organisms such as environmental samples, microbiome, mutant populations, or DNA libraries of microoganisms are plated to microbiological support media, with or without a membrane support which may be transferred from a media to an assay support at a microbial density that allows spatial distinction or localized enrichment of the bacteria on that support. Typically, an 85 mm Petri plate would display 300 to 3000 individual colonies; fewer or greater microbial colonies could be used.

The media may also be modified to be selective for various groups of microorganisms, such as salt tolerance (e.g., *Staphylococcus* growth on mannitol salt agar), or the addition of antibiotics such as cyclohexamide and nystatin at various concentrations (e.g., for selective growth of Actinomycetes and *Streptomyces* by addition of various antibiotics known to those skilled in the arts; Williams and Davies 1965, Use of antibiotics for selective isolation and enumeration of Actinomycetes in soil, J. Gen. Microbiol. 38: 251-261; Zhang, J. 2011, Improvement of an isolation medium for Actinomycetes. Modern Applied Science. 5 (2) 124-127; Seong et al., 2001, An improved selective isolation of rare Actinomycetes from forest soil, The Journal of Microbiology 39: 17-23), or the isolation of *Propionibacterium* on lactate and other isolation techniques (Kreig, 1981, Chapter 8, Enrichment and Isolation, p. 112-142 in Manual of Methods for General Bacteriology, Gerhardt et al., eds, American Society for Microbiology, Washington, D.C.).

Growth conditions may also be varied, including temperatures above the normal body temperature (e.g., 37 C for humans) such as 42 C, or below normal temperature such as 30 C. The atmospheric conditions of oxygen may be normal atmospheric, microaerophilic, hypoxic or anaerobic.

One or more media may be employed in one or more environmental conditions for the same biological sample, subdivided for each of the media and conditions. By way of example, a mixed bacterial population of the human skin microbiome is obtained by a skin swab plated at a density of approximately 1000 bacterial colonies per 85 mm Petri plate with tryptic soy agar media incubated in a 5% C02/air chamber at 35 C for 16 hours. The tryptic soy agar (Difco Manual Difco & BBL Manual: Manual of Microbiological Culture Media, Second Edition, M. J. Zimbro et al., (Eds), Becton Dickinson and Co., 2009).

The procedure of Example 1 is modified for neutrophil serine protease elastase inhibitors as indicated in Table 2.

Example 6: Enhanced Production of Protease Inhibitors

The bacteria may be further selected for enhanced protease inhibitor production. The methods described herein include a culture-based method for the isolation of microorganisms producing protease inhibitors. The production of the protease inhibitors is visualized on a petri dish (FIGS. 5A and 5B). Using methods known to those skilled in the arts which include various mutagenesis methods such as exposure to ultraviolet light, chemical mutagens such as nitrosoguanidine, or genetic methods such as overexpression by plasmids or introduction of strong promoters, transposon mutagenesis, organisms with improved production of protease inhibitors are visualized as producing more intensely staining zone of protease protection.

In order to develop strains with advantageous properties, biological, chemical or physical mutagens may be provided to generate new strains not preexisting in the source sample. The microbes may be recognized, for example, by their enhanced ability to secrete protease inhibitors. For example, a sample of purified or mixed bacteria may be subjected to radiation, such as ultraviolet light or gamma radiation, or chemical mutagens (Kodym, A. and Afzar, R. 2003, Physical and chemical mutagenesis. Methods in Molecular Biology 236: 189-204), to produce mutants, which can then be cultured and subcultured to select mutants with desired properties. Alternatively, the microbes may be altered by directed evolution (Lutz, S. 2010. Beyond directed evolution—semi-rational protein engineering and design. Curr. Opin. Biotechnol. 21: 734-743; Cai, W. et al., 2014. Directed evolution of three-finger toxin to produce serine protease inhibitors. J. Recept. Signal Transduct. Res. 34: 154-161). Likewise, the bacteria may be subject to the methods described by Pawelek et al., WO 96/40238, expressly incorporated herein by reference. The bacteria may be subject to genetic exchange technologies with natural or synthetic DNA from various sources (Vergunst, A and O'Callaghan, D. (eds) 2014, Host-Bacteria Interactions: Methods and Protocols. Methods in Molecular Biology 1197: 366 p.; Chaparro-Riggers, J. F. et al., 2007, Better library design: data driven protein engineering. Biotechnol. J. 2: 180-191), such as plasmids, transposons (Pajunen, M. I. et al., 2005. Generation of transposing insertion mutant libraries for gram-positive bacteria by electroporation of phage Mu DNA transposition complexes. Microbiology 151: 1209-1218), co-cultured strains, and the like. The result is various populations of bacteria that are distinct from their parent strains, some small portion of which may have properties which are considered advantageous by the selection process.

Example 7: Identification of Novel Secreted Protease Inhibitors

The secreted protease inhibitors as derived in the Examples identified above are inherently capable of secreting a protease inhibitor into the media. Supernatants of the media containing the protease are collected by centrifuging the bacteria and passing the supernatant through a 0.22 µm filter. Then, in a novel modification of protease zymography (Lantz and Ciborowski 1994, Zymographic techniques for detection and characterization of microbial proteases. Methods Enzymol. 1994; 235:563-594), a native, non-denaturing gel containing the cognate protein gelatin is run in duplicate, one with embedded gelatin and one without embedded gelatin. Rather than running a protease in the gel, the protease inhibitor supernatant is run. For the gelatin-embedded gel, the gel is then incubated in the exoenzyme protease supernatant which then digests all of the gelatin protein, except at the location of the protein band of the peptide protease inhibitor, which is determined by developing in 15% TCA (Hanspal et al., 1983, Detection of protease inhibitors using substrate-containing sodium dodecyl sulfate-polyacrylamide gel electrophoresis, Anal Biochem. 132 (2): 288-293). The duplicate gel is stained, the appropriate corresponding gel band is excised from the gel. The protein is identified using MALD-TOF.

Other protease inhibition assays based on individual clones or strains are already known to those skilled in the arts, and generally couple a biochemical test for proteolysis with purified fractions that potentially contain protease inhibitors. The protease inhibition assays as conducted by Wee et al. (2000) for identification of the *P. luminescens* protease inhibitor utilizes ammonium sulfate precipitation of the culture supernatant, redisolution of the precipitate in phosphate buffer, dialysis, separation by isoelectric focusing, and then testing of fractions for inhibitory activity using azocoll (Chavira et al., 1984 Assaying proteases with azocoll, Analytical Biochem. 136: 446-450). Inhibitory activity can also be monitored by determining hydrolysis of the chromogenic peptide N-a-benzoyl-DL-arginine-p-nitroanilide (BAPNA) or by following the change in absorbance at 275 nm of the protease substrate $N^\alpha$-p-tosyl-L-argininemethylester. The purified protease inhibitor is then identified by MALDI-TOF (Webster and Oxley 2012, Protein identification by MALDI-TOF mass spectrometry, Methods in Molecular Biology 2012; 800:227-40. doi: 10.1007/978-1-61779-349-3_15; Yukihira et al., 2010 MALDI-MS-based high-throughput metabolite analysis for intracellular metabolic dynamics, Analytical Chemistry, 15; 82(10):4278-82. doi: 10.1021/ac100024w).

Example 8: Genetically Engineering Bacteria to Produce Bacteriocins

Methods known to those skilled in the arts are used, including those described by Bermudes et al. U.S. Pat. No. 7,452,531 Compositions and Methods for Tumor-Targeted Delivery of Effector Molecules, expressly incorporated herein by reference in its entirety.

Example 9: Selection of Bacterial Strains with Enhanced Production of Bacteriocins The bacteria may be further selected for enhanced bacteriocin production using standard methods for visualizing production of bacteriocins which uses an indicator strain usually embedded in a soft agar overlay, and a test strain, or library of strains, applied to the surface. The production of the bacteriocin is then visualized as an increased zone of inhibition of the indicator strain. Using methods known to those skilled in the arts which include various mutagenesis methods such as exposure to ultraviolet light, chemical mutagens such as nitrosoguanidine, or genetic methods such as introduction of strong promoters, overexpression on plasmids, transposon mutagenesis, organisms with improved production of bacteriocins are visualized as producing wider zones of bacterial inhibition.

Example 10: Construction of *Propionibacterium acnes* Strains for Treatment of Acne Vulgaris

*Propionibacterium acnes*, such as RT6, is genetically engineered to express one or more bacteriocins that kill pathogenic *Propionibacterium acnes* using methods known to those skilled in the arts. The bacteria may be further selected for enhanced bacteriocin production using standard methods for visualizing production of bacteriocins which uses an indicator strain usually embedded in a soft agar overlay, and a test strain, or library or mixed population of strains, applied to the surface. The indicator strains are pathogenic bacteria, such as *Staphylococcus aureus*, *Streptococcus pyogenes*, or *Propionibacterium acnes* pathogenic ribotypes. The production of the bacteriocin is then visualized as an increased zone of inhibition of the indicator strain. Using methods known to those skilled in the arts which include various mutagenesis methods such as exposure to ultraviolet light, chemical mutagens such as nitrosoguanidine, or genetic methods such as over expression on plasmids, insertion of strong promoters, transposon mutagenesis, organisms with improved production of bacteriocins are visualized as producing wider zones of bacterial inhibition. Using similar techniques, the therapeutic *Propionibacterium* is selected for resistance to the pathogen bacteriocins, such as those of pathogenic *Propionibacterium* ribotypes.

The bacteria are further engineered to have phage resistance proteins, such as phage repressor proteins related to lambda phage c1 repressor, including those identified by Marinelli, et al., 2012 (*Propionibacterium acnes* Bacteriophages Display Limited Genetic Diversity and Broad Killing Activity against Bacterial Skin Isolates, mBio 3(5) doi: 10.1128/mBio.00279-1).

Use of standard methods of isolating and/or identifying phage resistant strains is also encompassed. It is of importance that the therapeutic bacterial strain, such as the RT6 strain of *Propionibacterium acnes*, be resistant to the resident, disease-associated organisms such as pathogenic ribotypes RT4, 5, 7, 8, 9 and 10 of *Propionibacterium acnes* (Fitz-Gibbon et al., 2013). Methods for selecting resistant strains selection for spontaneous resistance by exposure of the strain such as RT6 to the phage such as those described by Marinelli, et al., 2012 (*Propionibacterium acnes* Bacteriophages Display Limited Genetic Diversity and Broad Killing Activity against Bacterial Skin Isolates, mBio 3(5) doi:10.1128/mBio.00279-1), and recovery of the survivors, or the strain can be initially modified by chemical, ultraviolet or transposon mutagenesis, to create a mixed genetic population followed by exposure to the phage, and selection of survivors (Levin, 1994, Isolating multiple strains of *Escherichia coli* for coliphage isolation, phage typing, and mutant recovery, Chapter 4 pages 63-72, in Tested studies for laboratory teaching, Volume 15 (C. A. Goldman, Editor). Proceedings of the 15th Workshop/Conference of the Association for Biology Laboratory Education (ABLE), 390 pages; Exploitation of a new flagellatropic phage of *Erwinia* for positive selection of bacterial mutants attenuated in plant virulence: towards phage therapy T. J. Evans J Appl Microbiol 108 (2010) 676-685). The surviving strains may contain genetically integrated phage, i.e., lysogens. Preferred strains are those that do not contain the phage, which is readily determinable by genetic techniques such as PCR.

The resulting bacteria are both capable of resisting attack by the virulent bacterial bacteriocins and/or their phage, are able to persist, colonize and kill pathogenic strains by expressing bacteriocins the pathogenic strains are sensitive to, and secrete protease inhibitors that suppress inflammation.

Example 11: Treatment of Disease Using Purified Protease Inhibitors

Following identification and purification protease inhibitors, the inhibitors may be used for the treatment of protease-mediated diseases. By way of example, the purified protease inhibitor such as a chymase inhibitor or pathogenic *Propionibacterium* inhibitor is formulated in to an acceptable pharmaceutical carrier known to those skilled in the arts such as a cream, ointment or gel. The inhibitor is applied in sufficient frequency to eliminate the symptoms to a patient with dermatitis.

Example 12. Use of Microbiome Bacteria for the Treatment of Psoriasis, Acne Vulgaris, or Other Inflammatory Skin Diseases The purified protease inhibitor bacteria are used for treatment of psoriasis or acne vulgaris, for example. A sufficient amount of the bacteria are applied to the affected sites in a saline, gel cream or ointment formulation to result in colonization and inhibition of the inflammatory response, resulting in decrease in the size and/or number of inflammatory lesions.

A sufficient amount of the bacteria are applied to the affected sites in a pharmaceutically acceptable formulation such as saline, gel, cream or ointment to result in colonization and inhibition of the inflammatory response, resulting in decrease in the size and/or number of inflammatory lesions.

In general, the dosage ranges from about 1.0 cfu/kg to about $1 \times 10^{10}$c fu/kg; optionally from about 1.0 cfu/kg to about $1 \times 10^8$ cfu/kg; optionally from about $1 \times 10^2$ cfu/kg to about $1 \times 10^8$ cfu/kg; optionally from about $1 \times 10^4$ cfu/kg to about $1 \times 10^8$ cfu/kg.

Example 13. Use of Protease Inhibitor for the Treatment of Psoriasis or Acne Vulgaris The purified protease inhibitor proteins are used for treatment of psoriasis. A sufficient amount of the substantially purified protease inhibitor, obtained using standard protein purification procedures known to those skilled in the art, is applied to the affected sites in a pharmaceutically acceptable carrier such as saline, gel, cream or ointment formulation to result in inhibition of the inflammatory response, resulting in decrease in the size and/or number of inflammatory lesions.

Example 14: Identification of Microbiome Bacteria Secreting Protease Inhibitors

Secreted protease inhibitors of the human microbiome are determined from individual bacteria or mixed colonies of bacteria collected from human body sites by culturing the bacteria and screening for zones of protease inhibition. First, the cognate protein, e.g., collagen, or collagen fragments (gelatin), is embedded into a nutrient agar using methods known to those skilled in the arts. Second, a proteolytic bacterium of the human microbiome is grown under conditions for which it produces an exoenzyme protease, such as that for collagen or gelatin, the secretion of such which can be determined using the said gelatin-containing agar plate (Vermelho et al., 1996, Detection of Extracellular Proteases from Microorganisms on Agar Plates Mem Inst Oswaldo Cruz, Rio de Janeiro, Vol. 91(6): 755-760). Non-proteolytic bacteria are incubated on the gelatin agar plate, which may be a mixed culture including known or unknown organisms, and then replica plated to generate a master plate, to later recover bacteria of interest. The gelatin plate is then flooded with the exoenzyme protease supernatant and incubated for a sufficient time to degrade all of the gelatin embedded within the plate. The protease plate is then "developed" by precipitating undigested protein using 15% trichloroacetic acid (TCA). For microbiome bacteria secreting protease inhibitors, a halo of precipitated, undigested protein is observed due the presence of a protease inhibitor, and the corresponding bacterium selected from the master plate.

It will be understood that the foregoing is only illustrative of the principles of the invention, and that various modifications can be made by those skilled in the art without departing from the scope and spirit of the invention.

What is claimed is:

1. A pharmaceutical formulation in a topically-applied dosage form, for treatment of a human or animal, comprising:
   a bacteria that releases or secretes a protease inhibitor which reduces inflammation of at least one of skin and mucus membranes in a human or animal,
   the bacteria being of a type isolated from a human or animal microbiome source which does not release or secrete the protease inhibitor, subjected to at least one of guided evolution or mutagenesis to produce a defined change in the genome of the bacteria to cause release or secretion of the protease inhibitor, which has been selected for production of the protease inhibitor.

2. The pharmaceutical formulation according to claim 1, wherein the selection for production of the protease inhibitor comprises:
   growing a mixed population of microorganisms on protease-detection media;
   adding a protease followed by at least one antibiotic; and
   detecting protease inhibition.

3. The pharmaceutical formulation according to claim 1, wherein a dose of the topically-applied dosage form comprises a sufficient amount of the bacteria which release or secrete the protease inhibitor for avoidance of host immune response suppression of replication of the bacteria before achieving therapeutic levels for treatment of a human having at least one inflammation associated from a disorder selected from the group consisting of acne, psoriasis, atopic dermatitis, eczema and inflammatory bowel disease.

4. The pharmaceutical formulation according to claim 1, wherein the human or animal microbiome source comprises a microorganism selected from the group consisting of *Pseudomonas aeruginosa, Staphylococcus aureus, Staphylococcus caprae, Staphylococcus epidermidis, Streptococcus pyogenes, Candida albicans, Proteus* species, *Bacillus* species, *Clostridium* species, *Serratia* species, *Campylobacter, Streptomyces* species, *Porphromonas gingivalis, Lactococcus lactis, Lactococcus casei, Lactobacillus acidophilus, Streptococcus salivarus, Propionibacterium* species, *Corynebacterium* species, *Escherichia coli, Streptococcus agalaciae*, and *Listeria monocytogenes*.

5. The pharmaceutical formulation according to claim 1, wherein the protease inhibitor is inhibitory of at least one of chymase, calpain, Casp-1, or neutrophil elastase.

6. The pharmaceutical formulation according to claim 1, wherein the dosage form comprises the bacteria in live and replicatively competent form, which produce the protease inhibitor after administration to the at least one of the skin and mucous membranes of the human or animal.

7. The pharmaceutical formulation according to claim 6, wherein the bacteria in live and replicatively competent form are adapted to colonize human tissue after administration of the topically-applied dosage form.

8. The pharmaceutical formulation according to claim 6, wherein the bacteria in live form are produced by a process comprising:
   growing colonies of at least one type of bacteria derived from a mixed population of bacteria isolated from the human or animal microbiome source which does not produce the protease inhibitor on protease-detection media;
   adding a protease followed by an antibiotic treatment, such that no colonies of the at least one type of bacteria derived from the mixed population of bacteria isolated from the human or animal microbiome source which does not produce the protease inhibitor undergo additional growth in the presence of the protease on the protease detection media;
   subjecting the colonies of the at least one type of bacteria derived from the mixed population of bacteria isolated from the human or animal microbiome source which does not produce the protease inhibitor to at least one of guided evolution or mutagenesis;
   detecting enhanced inhibition of the protease by colonies of the at least one type of bacteria subjected to the at least one of guided evolution or mutagenesis; and
   selecting at least one colony comprising the live bacterium subjected to the at least one of guided evolution or mutagenesis based on the detected protease inhibition,
   wherein the at least one of guided evolution or mutagenesis of at least one colony of the at least one type of bacteria produces a change in the genome of the at least one colony of the at least one type of bacteria to cause release or secretion of the protease inhibitor.

9. A bacterium produced by a process comprising:
   growing colonies of bacteria derived from a mixed population of bacteria isolated from a human or animal microbiome source that does not produce a protease inhibitor on protease-detection media;

adding a protease followed by an antibiotic treatment, such that no colonies of the bacteria derived from a mixed population of bacteria isolated from a human or animal microbiome source that does not produce a protease inhibitor undergo additional growth in the presence of the protease on the protease detection media;

subjecting colonies of the mixed population of bacteria isolated from a human or animal microbiome source that does not produce a protease inhibitor to at least one of guided evolution or mutagenesis;

detecting enhanced inhibition of the protease by a protease inhibitor released or secreted by at least one bacterium subjected to the at least one of the guided evolution or mutagenesis, caused by the at least one of guided evolution or mutagenesis selecting at least one bacterium which releases or secretes the protease inhibitor based on the detected protease inhibition.

10. The bacterium according to claim 9, wherein the bacterium concurrently expresses a combination of the protease inhibitor and a bacteriocin that facilitates colonization of a target tissue of a human or an animal by the bacteria.

11. The bacterium according to claim 10, wherein the target tissue is selected from the group consisting of: skin exhibiting symptoms of psoriasis, skin exhibiting symptoms of atopic dermatitis, skin exhibiting symptoms of eczema, skin exhibiting symptoms of acne, and skin exhibiting symptoms of psoriasis.

12. The bacterium according to claim 9, wherein the bacterium produces the protease inhibitor selected from the group consisting of an inhibitor of at least one of chymase, calpain, Casp-1, proteases from *Staphylococcus aureus*, and neutrophil serine protease elastase.

13. The bacterium according to claim 9, wherein the bacterium produces a protease inhibitor that reduces inflammation of at least one of skin and mucus membranes in a human or animal.

14. The bacterium according to claim 9, provided as a living replicatively competent bacterium in a pharmaceutical formulation in dosage form, for treatment of a human or animal.

15. The bacterium according to claim 14, wherein the bacterium comprises a probiotic bacterium which colonizes at least one of human skin, human mucous membranes, and human gut, substantially without causing disease in healthy adult humans, and which replicates and releases or secretes the protease inhibitor in situ after administration to the human.

16. The bacterium according to claim 9, being a species selected from the group consisting of: *Pseudomonas aeruginosa, Staphylococcus aureus, Staphylococcus caprae, Staphylococcus epidermidis, Streptococcus pyogenes, Candida albicans, Proteus* species, *Bacillus* species, *Clostridium* species, *Serratia* species, *Campylobacter, Streptomyces* species, *Porphromonas gingivalis, Lactococcus lactis, Lactococcus casei, Lactobacillus acidophilus, Streptococcus salivarus, Propionibacterium* sp, *Corynebacterium* species, *Escherichia coli, Streptococcus agalaciae*, and *Listeria monocytogenes*.

17. A pharmaceutical formulation dosage form for treatment of skin or mucous membranes of a human or animal, comprising human or animal microbiome-derived bacteria that express a protease inhibitor which inhibits at least one of chymase, calpain, Casp-1, or elastase, that reduces inflammation of at least one of the skin and the mucus membranes in the human or animal, the human or animal microbiome-derived bacteria being subjected to at least one of guided evolution or mutagenesis to produce a defined change in the genome which causes release or secretion of the protease inhibitor not released or secreted by the human or animal microbiome-derived bacteria, which are selected for production of the protease inhibitor and wherein the human or animal microbiome-derived bacteria being of genus *Pseudomonas, Staphylococcus, Streptococcus, Candida, Proteus, Bacillus, Clostridium, Serratia, Campylobacter, Streptomyces, Porphromonas, Lactococcus, Lactobacillus, Propionibacterium, Corynebacterium, Escherichia*, or *Listeria*.

18. The pharmaceutical formulation dosage form according to claim 4, comprising a sufficient amount of the bacteria which release or secrete the protease inhibitor for avoidance of host immune response suppression of replication of the bacteria before achieving therapeutic levels for treatment of a human having at least one inflammation associated from a disorder selected from the group consisting of acne, psoriasis, atopic dermatitis, eczema and inflammatory bowel disease.

19. The pharmaceutical formulation dosage form according to claim 17, wherein the bacteria concurrently express a combination of the protease inhibitor and a bacteriocin that facilitates colonization of the skin or mucous membranes of a human or an animal.

20. The pharmaceutical formulation dosage form according to claim 17, adapted to treat at least one of skin exhibiting symptoms of psoriasis, skin exhibiting symptoms of atopic dermatitis, skin exhibiting symptoms of eczema, skin exhibiting symptoms of acne, and skin exhibiting symptoms of psoriasis.

* * * * *

SEQUENCE LISTING

```
<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: ZOT domain aa 288-293

<400> SEQUENCE: 1

Phe Cys Ile Gly Arg Leu
1               5

<210> SEQ ID NO 2
<211> LENGTH: 7
<212> TYPE: PRT
<213> ORGANISM: Artificial Sequence
<220> FEATURE:
<223> OTHER INFORMATION: submandibular gland peptide-T

<400> SEQUENCE: 2

Thr Asp Ile Phe Glu Gly Gly
1               5

<210> SEQ ID NO 3
<211> LENGTH: 10
<212> TYPE: PRT
<213> ORGANISM: Artificial Sequence
<220> FEATURE:
<223> OTHER INFORMATION: short peptide inhibitory to MMP2 and MMP9

<400> SEQUENCE: 3

Cys Thr Thr His Trp Gly Phe Thr Leu Cys
1               5                   10

<210> SEQ ID NO 4
<211> LENGTH: 4
<212> TYPE: PRT
<213> ORGANISM: Artificial Sequence
<220> FEATURE:
<223> OTHER INFORMATION: leukocyte specific ?-2 integrin binding partner
      for pro-MMP-9

<400> SEQUENCE: 4

Asp Asp Gly Trp
1

<210> SEQ ID NO 5
<211> LENGTH: 4
<212> TYPE: PRT
<213> ORGANISM: Artificial Sequence
<220> FEATURE:
```

```
<223> OTHER INFORMATION: Chymase substrate N-Succinyl-Ala-Ala-Pro-Phe
      p-nitroanilide

<400> SEQUENCE: 5

Ala Ala Pro Phe
1

<210> SEQ ID NO 6
<211> LENGTH: 4
<212> TYPE: PRT
<213> ORGANISM: Artificial Sequence
<220> FEATURE:
<223> OTHER INFORMATION: Chymas Protease inhibitor Z-Arg-Glu-Thr-Phep
      Phe p (OPh)2

<400> SEQUENCE: 6

Arg Gln Thr Phe
1

<210> SEQ ID NO 7
<211> LENGTH: 4
<212> TYPE: PRT
<213> ORGANISM: Artificial Sequence
<220> FEATURE:
<223> OTHER INFORMATION: Calpain substrate Suc-LLVY-aminoluciferin

<400> SEQUENCE: 7

Leu Leu Val Tyr
1

<210> SEQ ID NO 8
<211> LENGTH: 4
<212> TYPE: PRT
<213> ORGANISM: Artificial Sequence
<220> FEATURE:
<223> OTHER INFORMATION: Furin substrate Boc-Arg-Val-Arg-Arg-AMC

<400> SEQUENCE: 8

Arg Val Arg Arg
1

<210> SEQ ID NO 9
<211> LENGTH: 4
<212> TYPE: PRT
<213> ORGANISM: Artificial Sequence
<220> FEATURE:
<223> OTHER INFORMATION: Furin Inhibitor I N2-(Decanoyl-RVKR-CMK)

<400> SEQUENCE: 9

Arg Val Lys Arg
1

<210> SEQ ID NO 10
<211> LENGTH: 4
<212> TYPE: PRT
<213> ORGANISM: Artificial Sequence
<220> FEATURE:
<223> OTHER INFORMATION: Casp-1 substrate YVAD-AFC

<400> SEQUENCE: 10

Tyr Val Ala Asp
1

<210> SEQ ID NO 11
<211> LENGTH: 4
<212> TYPE: PRT
<213> ORGANISM: Artificial Sequence
```

```
<220> FEATURE:
<223> OTHER INFORMATION: Caspase-1 Inhibitor VI (Z-YVAD-FMK)

<400> SEQUENCE: 11

Tyr Val Ala Asp
1

<210> SEQ ID NO 12
<211> LENGTH: 5
<212> TYPE: PRT
<213> ORGANISM: Artificial Sequence
<220> FEATURE:
<223> OTHER INFORMATION: MMP-2/MMP-9 Substrate II
      Ac-Pro-Leu-Gly-(2-mercapto-4-methylpentanoyl)-Leu-Gly-OEt

<400> SEQUENCE: 12

Pro Leu Gly Leu Gly
1               5
```